US007851212B2

(12) United States Patent
Berinstein et al.

(10) Patent No.: US 7,851,212 B2
(45) Date of Patent: Dec. 14, 2010

(54) IMMUNOGENIC POLYPEPTIDES ENCODED BY MAGE MINIGENES AND USES THEREOF

(75) Inventors: Neil Berinstein, Toronto (CA); James Tartaglia, Aurora (CA); John A. Tine, Scotia, NY (US); Philippe Moingeon, Pommiers (FR); Thierry Boon-Falleur, Brussels (BE); Pierre Vander Bruggen, Brussels (BE)

(73) Assignees: Sanofi Pasteur Limited, North York, Ontario (CA); Ludwig Institute for Cancer Research, Brussels (BE)

( * ) Notice: Subject to any disclaimer, the term of this patent is extended or adjusted under 35 U.S.C. 154(b) by 1184 days.

(21) Appl. No.: 10/275,993

(22) PCT Filed: May 7, 2001

(86) PCT No.: PCT/CA01/00646

§ 371 (c)(1), (2), (4) Date: Jul. 8, 2003

(87) PCT Pub. No.: WO01/85932

PCT Pub. Date: Nov. 15, 2001

(65) Prior Publication Data

US 2004/0033234 A1   Feb. 19, 2004

Related U.S. Application Data

(60) Provisional application No. 60/202,970, filed on May 10, 2000, provisional application No. 60/203,578, filed on May 11, 2000, provisional application No. 60/242,388, filed on Oct. 20, 2000.

(51) Int. Cl.
   *C12N 15/63* (2006.01)
(52) U.S. Cl. .................................. 435/320.1; 536/23.1
(58) Field of Classification Search .............. 435/320.1; 536/23.1
   See application file for complete search history.

(56) References Cited

U.S. PATENT DOCUMENTS

| | | | |
|---|---|---|---|
| 4,603,112 A | 7/1986 | Paoletti et al. |
| 4,722,848 A | 2/1988 | Paoletti et al. |
| 4,769,330 A | 9/1988 | Paoletti et al. |
| 4,882,278 A | 11/1989 | Mekalanos |
| 4,923,808 A | 5/1990 | Matteucci |
| 4,956,281 A | 9/1990 | Wallner et al. |
| 5,093,258 A | 3/1992 | Cohen et al. |
| 5,110,587 A | 5/1992 | Paoletti et al. |
| 5,141,742 A | 8/1992 | Brown et al. |
| 5,155,020 A | 10/1992 | Paoletti et al. |
| 5,174,993 A | 12/1992 | Paoletti et al. |
| 5,185,146 A | 2/1993 | Altenburger |
| 5,204,243 A | 4/1993 | Paoletti et al. |
| 5,225,336 A | 7/1993 | Paoletti et al. |
| 5,279,833 A | 1/1994 | Rose |
| 5,283,185 A | 2/1994 | Epand et al. |
| 5,342,774 A | 8/1994 | Boon et al. |
| 5,364,773 A | 11/1994 | Paoletti et al. |
| 5,378,457 A | 1/1995 | Paoletti et al. |
| 5,405,940 A | 4/1995 | Boon et al. |
| 5,453,364 A | 9/1995 | Paoletti |
| 5,462,871 A | 10/1995 | Boon-Falleur et al. |
| 5,494,807 A | 2/1996 | Paoletti et al. |
| 5,504,005 A | 4/1996 | Bloom et al. |
| 5,505,941 A | 4/1996 | Paoletti et al. |
| 5,527,928 A | 6/1996 | Nantz et al. |
| 5,554,506 A | 9/1996 | van der Bruggen et al. |
| 5,554,724 A | 9/1996 | Melief et al. |
| 5,585,461 A | 12/1996 | Townsend et al. |
| 5,589,466 A | 12/1996 | Felgner et al. |
| 5,591,430 A | 1/1997 | Townsend et al. |
| 5,631,010 A | 5/1997 | Mekalanos |
| 5,651,981 A | 7/1997 | Ashley et al. |
| 5,662,907 A | 9/1997 | Kubo et al. |
| 5,679,647 A | 10/1997 | Carson et al. |
| 5,686,068 A | 11/1997 | Melief et al. |
| 5,695,994 A | 12/1997 | Boon-Falleur et al. |
| 5,698,530 A | 12/1997 | Schlom |
| 5,703,055 A | 12/1997 | Felgner et al. |
| 5,707,618 A | 1/1998 | Armentano et al. |
| 5,739,026 A | 4/1998 | Garoff et al. |
| 5,747,028 A | 5/1998 | Calderwood et al. |

(Continued)

FOREIGN PATENT DOCUMENTS

WO      WO 91/11194 A1      8/1991

(Continued)

OTHER PUBLICATIONS

Herbert et al. (The Dictionary of Immunology, Academic Press, 4th edition, 1995, p. 58).*
Greenspan et al. 1999. Nature Biotechnology 7:936-937.*
Stites et al, 1997, 9th ed, Medical Immunology, p. 50-52).*
Kawashima et al, Human Immunol, 1998, 59(1): 1-14.*
van der Bruggen et al, 1991, Science, 254: 1643-1647.*
Westby et al, 1992, Bioconjugate Biochem, 3(5): 375-81.*
Hu, et al. 1996. Enhancement of Cytolytic T Lymphocyte Precursor Frequency in Melanoma Patients following Immunization with the MAGE-1 Peptide . . . Cancer Res. 56: 2479-2483.
Van Der Bruggen, et al. 1991. A Gene Encoding an Antigen Recognized by Cytolytic T Lymphocytes on a Human Melanoma. Science, 254: 1643-1647.

(Continued)

*Primary Examiner*—Larry R. Helms
*Assistant Examiner*—Minh-Tam Davis
(74) *Attorney, Agent, or Firm*—Patrick J. Halloran

(57) ABSTRACT

The invention discloses immunogenic polypeptides comprising several MAGE-specific antigen epitopes selected from different (i.e. discrete) members of the MAGE protein family, nucleic acids coding therefor, recombinant viruses and/or cells comprising said nucleic acids, and compositions thereof. Methods for eliciting or inducing MAGE-specific immune responses utilizing the aforementioned immunogenic agents are also disclosed.

14 Claims, 6 Drawing Sheets

U.S. PATENT DOCUMENTS

| | | |
|---|---|---|
| 5,756,103 A | 5/1998 | Paoletti et al. |
| 5,762,938 A | 6/1998 | Paoletti et al. |
| 5,766,599 A | 6/1998 | Paoletti et al. |
| 5,789,245 A | 8/1998 | Dubensky et al. |
| 5,792,462 A | 8/1998 | Johnston et al. |
| 5,804,566 A | 9/1998 | Carson et al. |
| 5,830,877 A | 11/1998 | Carson et al. |
| 5,831,016 A | 11/1998 | Wang et al. |
| 5,833,975 A | 11/1998 | Paoletti et al. |
| 5,840,839 A | 11/1998 | Wang et al. |
| 5,843,448 A | 12/1998 | Chen et al. |
| 5,843,723 A | 12/1998 | Dubensky et al. |
| 5,844,075 A | 12/1998 | Kawakami et al. |
| 5,851,523 A | 12/1998 | Townsend et al. |
| 5,871,727 A | 2/1999 | Curiel |
| 5,874,560 A | 2/1999 | Kawakami et al. |
| 5,919,676 A | 7/1999 | Graham et al. |
| 5,932,210 A | 8/1999 | Gregory et al. |
| 5,942,235 A | 8/1999 | Paoletti |
| 5,965,535 A | 10/1999 | Chaux et al. |
| 5,972,597 A | 10/1999 | Paoletti et al. |
| 5,985,847 A | 11/1999 | Carson et al. |
| 5,990,091 A | 11/1999 | Tartaglia et al. |
| 5,994,132 A | 11/1999 | Chamberlain et al. |
| 5,994,136 A | 11/1999 | Naldini et al. |
| 6,001,349 A | 12/1999 | Panicali et al. |
| 6,013,516 A | 1/2000 | Verma et al. |
| 6,019,987 A | 2/2000 | van der Bruggen |
| 6,025,474 A | 2/2000 | Van den Eynde et al. |
| 6,037,135 A | 3/2000 | Kubo et al. |
| 6,045,802 A | 4/2000 | Schlom et al. |
| 6,057,158 A | 5/2000 | Chamberlain et al. |
| 6,083,703 A | 7/2000 | Wang et al. |
| 6,087,110 A | 7/2000 | Wang et al. |
| 6,127,116 A | 10/2000 | Rice et al. |
| 6,132,980 A | 10/2000 | Wang et al. |
| 6,171,855 B1 | 1/2001 | Askari |
| 6,224,879 B1 | 5/2001 | Sjoberg et al. |
| 6,228,621 B1 | 5/2001 | Williams et al. |
| 6,235,522 B1 | 5/2001 | Kingsman et al. |
| 6,245,333 B1 | 6/2001 | Coulie et al. |
| 6,277,633 B1 | 8/2001 | Olsen |
| 6,291,430 B1 * | 9/2001 | Chaux et al. ............... 514/13 |
| 6,319,496 B1 | 11/2001 | Panicali et al. |
| 6,340,462 B1 | 1/2002 | Paoletti et al. |
| 6,353,089 B1 | 3/2002 | van der Bruggen et al. |
| 6,407,063 B1 | 6/2002 | Warnier et al. |
| 6,511,800 B1 | 1/2003 | Parks et al. |
| 6,531,451 B1 | 3/2003 | Chaux et al. |
| 6,537,560 B1 | 3/2003 | Kawakami et al. |
| 6,548,068 B1 | 4/2003 | Schlom et al. |
| 6,555,107 B2 | 4/2003 | Poeschla et al. |
| 6,558,671 B1 | 5/2003 | Slingluff et al. |
| 6,566,093 B1 | 5/2003 | Liljestrom et al. |
| 6,599,699 B1 | 7/2003 | Gaugler et al. |
| 6,656,734 B1 | 12/2003 | Bischoff et al. |
| 6,693,086 B1 | 2/2004 | Dow et al. |
| 6,699,475 B1 | 3/2004 | Panicali et al. |
| 6,710,172 B1 | 3/2004 | Chaux et al. |
| 6,756,038 B1 | 6/2004 | Schlom et al. |
| 6,780,407 B1 | 8/2004 | Paoletti et al. |
| 6,805,869 B2 | 10/2004 | Guo |
| 6,893,869 B2 | 5/2005 | Schlom et al. |
| 6,951,917 B1 | 10/2005 | Topalian et al. |
| 6,969,609 B1 | 11/2005 | Schlom et al. |
| 7,211,432 B2 | 5/2007 | Schlom et al. |
| 7,232,887 B2 | 6/2007 | Kawakami et al. |
| 7,255,862 B1 | 8/2007 | Tartaglia et al. |
| 7,351,409 B2 | 4/2008 | Chaux et al. |
| 7,364,729 B2 | 4/2008 | Kundig et al. |
| 2001/0007659 A1 | 7/2001 | Wong-Staal et al. |
| 2002/0123471 A1 | 9/2002 | Uberla |
| 2003/0022854 A1 | 1/2003 | Dow et al. |
| 2003/0082150 A1 | 5/2003 | Boon-Falleur et al. |
| 2003/0113919 A1 | 6/2003 | Emtage et al. |
| 2004/0009185 A1 | 1/2004 | Emtage et al. |
| 2004/0156861 A1 | 8/2004 | Figdor et al. |
| 2005/0136066 A1 | 6/2005 | Guo |

FOREIGN PATENT DOCUMENTS

| | | |
|---|---|---|
| WO | WO 91/13157 | 9/1991 |
| WO | WO 92/01796 | 2/1992 |
| WO | WO 92/11354 | 7/1992 |
| WO | WO 96/11279 A2 | 4/1996 |
| WO | WO 96/26214 | 8/1996 |
| WO | WO 92/21376 | 12/1996 |
| WO | WO 97/15597 A1 | 5/1997 |
| WO | WO 97/31017 | 8/1997 |
| WO | WO 98/04728 A1 | 2/1998 |
| WO | WO 98/15636 | 4/1998 |
| WO | WO 98/29556 A1 | 7/1998 |
| WO | WO 98/39463 | 9/1998 |
| WO | WO 98/46083 | 10/1998 |
| WO | WO 99/19501 | 4/1999 |
| WO | WO 99/27101 | 6/1999 |
| WO | WO 99/30742 | 6/1999 |
| WO | WO 99/40188 A2 | 8/1999 |
| WO | WO 99/43839 A1 | 9/1999 |
| WO | WO 99/46988 | 9/1999 |
| WO | WO 99/46992 A1 | 9/1999 |
| WO | WO 01/30382 A1 | 5/2001 |
| WO | WO 01/30847 A1 | 5/2001 |
| WO | WO 03/080800 A2 | 10/2003 |

OTHER PUBLICATIONS

Van Der Eynde, et al. 1997. Tumor antigens recognized by T lymphocytes. Int. J. Clin. Lab. Res. 27: 81-86.

Toso, et al. 1996. MAGE-1-specific Precursor Cytotoxic T-Lymphocytes Present Among Tumor-infiltrating Lymphocytes from a Patient with Breast Cancer . . . Cancer Res. 56: 16-20.

Boon, et al. 1994. Tumor Antigens Recognized by T Lymphocytes. Ann. Rev. Immunol. 12:337-365.

De Plaen, et al. 1994. Structure, chromosomal location, and expression of 12 genes of the MAGE family. Immunogenetics 40: 360-369.

De Smet et al. 1994. Sequence and expression pattern of the human MAGE2 gene. Immunogenetics 39:121-129.

Takahashi et al. 1995. Identification of MAGE-1 and MAGE-4 Proteins in Spermatogonia and Primary Spermatocytes of Testis. Cancer Res. 55: 3478-3482.

Chomez et al. 1996. The SMAGE gene family is expressed in post-meiotic spermatids during mouse germ cell differentiation. Immunogenetics 43: 97-100.

Brasseur et al 1995. Expression of MAGE Genes in Primary and Metastatic Cutaneous Melanoma. Int. J. Cancer 63: 375-380.

Weynants et al. 1994. Expression of MAGE Genes by Non-Small-Cell Lung Carcinomas. Int. J. Cancer 59:826-829.

Eura et al. 1995. Expression of the MAGE Gene Family in Human Head-and-Neck Squamous Cell Carcinomas. Int. J. Cancer 64: 304-308.

Inoue et al. 1995. Human Esophageal Carcinomas Frequently Express The Tumor-Rejectoin Antigens of MAGE Genes. Int. J. Cancer 63: 523-526.

Patard et al. 1995. Expression of MAGE Genes in Transitional-Cell Carcinomas of the Urinary Bladder. Int. J. Cancer 64: 60-64.

Brasseur et al. 1992. Human gene MAGE-1, which codes for tumor-rejection antigen, is expressed by some breast tumors. Int. J. Cancer 52: 839-841.

Van Den Eynde, et al. 1995. New tumor antigens recognized by T cells. Curr. Opin. Immunol. 7: 674-681.

Traversi et al. 1992. A Nonapeptide Encoded by Human Gene MAGE-1 Is Recognized on HLA-A1 by Cytolytic T Lymphocytes Directed Against . . . Exp. Med. 176: 1453-1457.

Tanzarella et al. 1999. Identification of a Promiscuous T-Cell Epitope Encoded by Multiple Members of the MAGE Family. Cancer Res. 59: 2668-2674.

Van Der Bruggen et al. 1994. Autologous cytolytic T lymphocytes recognize a MAGE-1 nonapeptide on melanomas expressing HLA-Cw*1601*. Eur. J. Immunol. 24: 2134-2140.

Fujie et al. 1999. A MAGE-1-Encoded HLA-A24-Binding Synthetic Peptide Induces Specific Anti-Tumor Cytotoxic T Lymphocytes. Int. J. Cancer 80: 169-172.

Herman et al. 1996. A peptide encoded by the human MAGE3 gene and presented by HLA-B44 induces cytolytic T lymphocytes . . . Immunogenetics 43: 377-383.

Van Der Bruggen et al. 1994. A peptide encoded by human gene MAGE-3 and presented by HLA-A2 incudes cytolytic T lymphocytes . . . Eur. J. Immunol. 24: 3038-3043.

Chaux et al. 1999. Identification of Five MAGE-Al Epitopes Recognized by Cytolytic T Lymphocytes Obtained by In Vitro Stimulation . . . J Immunol. 163: 2928-2936.

Tartaglia et al. 1992. NYVAC: A Highly Attenuated Strain of Vaccinia Virus. Virology 188: 217-232.

Gaugler et al. 1994. Human Gene MAGE-3 Codes for an Antigen Recognized on a Melanoma by Autologous Cytolytic T Lymphocytes. J. Exp. Med. 179: 921-930.

Schultz et al. 2001. A MAGE-3 peptide recognized on HLA-B35 and HLA-A1 by cytolytic T lymphocytes. Tissue Antigens. 57: 103-109.

Tartaglia, et al. 1993. Protection of Cats against Feline Leukemia Virus by Vaccination with a Canarypox Virus Recombinant, ALVAC-FL. J. Virol. 67: 2370-2375.

Chamberlain, et al. Costimulation Enhances the Active Immunotherapy Effect of Anticancer Vaccines. Cancer Res. 56: 2832-2836 (1996).

Cox, et al. Identification of a peptide recognized by five melanoma-specific human cytotoxic T cell lines. Science, 264:716-719 (1994).

GenBank Accession No. J03132 (Mar. 25, 1988).
GenBank Accession No. M27533 (Sep. 8, 1989).
GenBank Accession No. X52264 (Aug. 28, 1989).
GenBank Accession No. X60958 (Jul. 18, 1991).
GenBank Accession No. Y00636 (Aug. 31, 1987).

Hodge, et al. Admixture of Recombinant Vaccinia Virus Containing the Gene for the Costimulatory Molecule B7 and a Recombinant Vaccinia Virus Containing a Tumor-associated Antigen Gene Results in Enhanced Specific T-Cell Responses and Antitumor Immunity. Cancer Res. 55: 3598-3603 (1995).

Hodge, et al, A Triad of Costimulatory Molecules Synergize to Amplify T-Cell Activation. Cancer Res. 59: 5800-5807 (1999).

Kawakami, et al. Identification of the immunodominant Peptides of the MART-1 Human Melanoma Antigen Recognized by the Majority of HLA-A2-restricted Tumor Infiltrating Lymphocytes. J. Exp. Med., 180:347-352 (1994).

Kawashima, et al The Multi-epitope Approach for Immunotherapy for Cancer: Identification of Several CTL Epitopes from Various Tumor-Associated Antigens Expressed on Solid Epithelial Tumors. Human Immunol. 59: 1-14 (1998).

Kocher, et al. Identification and Intracellular Location of MAGE-3 Gene Product. Cancer Res. 55: 2236-2239 (1995).

Maeurer, et al. New Treatment Options for Patients with Melanoma: Review of Melanoma-Derived T-Cell Epitope-Based Peptide Vaccines. Melanoma Res. 6: 11-24 (1996).

Marchand, et al. Tumor Regressions Observed in Patients with Metastatic Melanoma Treated with an Antigenic Peptide Encoded by Gene MAGE-3 and Presented by HLA-A1. Int. J. Cancer. 80: 219-230 (1999).

Mateo, et al. An HLA-A2 Polyepitope Vaccine for Melanoma Immunotherapy. J. Immunol. 163(7): 4058-4063 (1999).

Salgaller, et al. Immunization Against Epitopes in the Human Melanoma Antigen gp100 Following Patient Immunization with Synthetic Peptides. Cancer Res. 56: 4749-4757 (1996).

Tam, et al. Incorporation of T and B Epitopes of the Circumsporozite Protein in a Chemically Defined Synthetic Vaccine Against Malaria. J. Exp. Med. 171: 299-306 (1990).

Thomson, et al. Minimal Epitopes Expressed in a Recombinant Polyepitope Protein are Processed and Presented to CD8+ Cytotoxic T Cells: Implications for Vaccine Design. Proc. Natl. Acad. Sci. USA. 92: 5845-5849 (1995).

Thomson, et al. Delivery of Multiple CD8 Cytotoxic T Cell Epitopes by DNA Vaccination. J. Immunol. 160: 1717-1723 (1998).

Toes, et al. Protective Anti-Tumor Immunity Induced by Vaccination with Recombinant Adenoviruses Encoding Multiple Tumor-Associated Cytotoxic T Lymphocyte Epitopes in a String-of-Beads Fashion. Proc. Natl. Acad, Sci. USA. 94: 14660-14665 (1997).

Tuting, et al. Autologous Human Monocyte-Derived Dendritic Cells Genetically Modified to Express Melanoma Antigens Elicit Primary Cytotoxic T Cell Responses in vitro: Enhancement by Cotransfection of Genes Encoding the TH1 Biasing Cytokines IL-12 and IFN-alpha. J. Immunol. 160: 1139-1147 (1998).

Wang, et al. Utilization of an Alternative Open Reading Frame of a Normal Gene in Generating a Novel Human Cancer Antigen. J. Exp. Med. 186:1131-1140 (1996).

Xiang, et al. An Autologous Oral DNA Vaccine Protects Against Murine Melanoma. Proc. Natl. Acad. Sci. USA. 97(10): 5492-5497 (2000).

Bueler, H. and R. Mulligan. Mol. Medicine, 2(5): 545-555 (1996).

Aarts, et al, Vector-based Vaccine/Cytokine Conibination Therapy to Enhance Induction of Immune Responses to a Self-Antigen and Antitumor Activity. Cancer Res. 62: 5770-5777 (Oct. 15, 2002).

Ahlers, et al. Mechanisms of Cytokine Synergy Essential for Vaccine Protection Against Viral Challenge, Int. Immunol. 13(7): 897-908 (2000).

Anton, et al. Cytokines and Tumor Vaccination. Cancer Biotherapeutics and Radiopharmaceuticals. 11(5): 315-318 (1996).

Arch, et al. Hypopigmentation Associated with an Adenovirus-Mediated gp100/Mart-1 Transduced Dendritic Cell Vaccine for Metastatic Melanoma. Arch. Dermatol. 138(6): 799-802 (2002).

Astsaturov, et al. Amplification of Virus-induced Antimelanoma T-Cell Reactivity by High-Dose Interferon-Alpha 2b; Implications for Cancer Vaccines. Clin. Cancer Res. 9(12): 4347-4355 (2003).

Bakker, et al. Analogues of CTL epitopes with improved MHC class-I binding capacity elicit anti-melanoma CTL recognizing the wild-type epitope. Int. J. Cancer 70, 302-309 (1997).

Balch, et al. Final version of the American Joint Committee on Cancer staging system for cutaneous melanoma. *J. Clin. Oncol.* 19: 3635-3648 (2001).

Berinstein, et al. Carcinoembryonic Antigen as a Target for Therapeutic Anticancer Vaccines: A Review. J. Clin. Oncol. 20(8): 2197-2207 (2002).

Boel, et al. BAGE: A New Gene Encoding an Antigen Recognized on Human Melanomas by Cytolytic T Lymphocytes. Immunity, 2:167-175 (1995).

Brasseur, et al. Human Gene MAGE-1, Which Codes for a Tumor Antigen, is Expressed by Some Breast Tumors. Int. J. Cancer 52: 839-841 (1992).

Coulie, et al. A Mutated Intron Sequence Codes for an Antigenic Peptide Recognized by Cytotoxic T Lymphocytes on a Human Melanoma. PNAS USA, 92: 7976-7980 (1995).

Disis, et al. Granulocyte-Macrophage Colony-Stimulating Factor: An Effective Adjuvant for Protein and Peptide-Based Vaccines. Blood, 88(11): 202-210 (1996).

Dubensky, et al. Delivery Systems for Gene-Based Vaccines. Mol. Med. 6(9): 723-732 (2000).

Ellem, et al. The labyrinthine ways of cancer mununotherapy—T cell, tumor cell encounter; "how do I lose thee? Let me count the ways". Adv. Cancer Res. 75:203-49: 203-249 (1998).

Gramaglia, et al. Ox-40 Ligand: A Potent Costimulatory Molecule for Sustaining Primary CD4 T Cell Responses. J. Immunol. 161: 6510-6517 (1998).

Gurunathan, et al, CD4O Ligand/Trimer DNA Enhances Both Humoral and Cellular Immune Responses and Induces Protective Immunity to Infectious and Tumor Immunity. J. Immunol. 161: 4563-4571 (1998).

Haluska, et al. Immunologic Gene Therapy: A Phase I/II Trial Utilizing Autologous Dendritic Cells Transduced with gp100 and Melan A/MART-1 -Encoding Adenoviruses in Advanced Melanoma. Blood, 98(1): 694a-695a, Abstract 2903 (Nov. 16, 2001).

Hermonat, et al. Use of Adeno-Associated Virus as a Mammalian DNA Cloning Vector: Transduction of Neomycin Resistance Into Mammalian Tissue Culture Cells, PSNA USA, 81 6466-6470 (1984).

Herz, et al. Adenovirus-Mediated Transfer of Low Density Lipoprotein Receptor Gene Acutely Accelerates Cholesterol Clearance in Normal Mice, PNAS USA, 90: 2812-2816 (1993).

Hodge, et at. Diversified Prime and Boost Protocols Using Recombinant Vaccine Virus and Recombinant Non-Replicating Avian Pox Virus to Enhance T-Cell Immunity and Antitumor Responses. Vaccine, vol. 15, issue 6/7, pp. 759-768 (1997).

Horig, et al. Phase I Clinical Trial of Recombinant Canarypox (ALVAC) Vaccine Expressing Human Carcinoembryonic Antigen and B7.1 Costimulatory Molecule. Cancer Immunol. Immunother. 49: 504-514 (2000).

Hurpin, et al. The Mode of Presentation and Route of Administration Are Critical for the Induction of Immune Responses to p53 and Antitumor Immunity. Vaccine, vol. 16, No. 2/3, pp. 208-215 (1998).

Irvine, et al, Recombinant Virus Vaccination Against "Self" Antigens Using Anchor-Fixed Immunogens. Cancer Res., vol. 59: 2536-2540 (1999).

Jager, et al. Monitoring CD8 T Cell Responses to NY-ESO-1: Correlation of Humoral and Cellular Immune Responses. PNAS USA. 97(9): 4760-4765 (2000).

Karakinas, et al. Monoclonal Anti-MAGE-3 CTL Responses in Melanoma Patients Displaying Tumor Regression after Vaccination with a Recombinant Canarypox Virus. J. Immunol. 171: 4989-4904 (2003).

Kawakami, et al. Identification of a Human Melanoma Antigen Recognized by Tumor-Infiltrating Lymphocytes Associated with in vivo Tumor Rejection. Proc. Natl. Acad. Sci. USA, vol. 91, pp. 6458-6462 (1994).

Kirkwood, et al. Systemic Adjuvant Treatment of High-Risk Melanoma: the Role of Interferon Alfa-2b and Other Immunotherapies. Eur. J. Cancer, 34: 12-17 (1998).

Kirkwood, et al. High-Dose Interferon Alfa-2b Does Not Diminish Antibody Response to GM2 Vaccination in Patients With Resected Melanoma: Results of the Multicenter Eastern Cooperative Oncology Group Phase II Trial E2696, J. Clin Oncol. 19: 1430-1436 (2001).

Kirkwood, et al. High-Dose Interferon Alfa-2b Significantly Prolongs Relapse-Free and Overall Survival Compared With the GM2-KLH/QS-2I Vaccine in Patients With Resected Stage IIB-III Melanoma : Results of Intergroup Trial EI694/S9512/C509801. J. Clin. Oncol. 19: 2370-2380 (2001).

Leitner, et al. Enhancement of Tumor-Specific Immune Response with Plasmid DNA Replicon Vectors. Cancer Res. 60: 51-55 (2000).

Lindsey, et al. Impact of the Number of Treatment Courses on the Clinical Response of Patients Who Receive High-Dose Bolus Interleukin-2. J. Clin. Oncol. 18(9): 1954-1959 (2000).

Liu, et al. Gene-Based Vaccines. Mol. Ther. 1(6): 497-500 (2000).

Marshall, et al. Phase I Study in Advanced Cancer Patients of a Diversified Prime-And-Boost Vaccination Protocol Using Recombinant Vaccinia Virus and Recombinant Nonreplicating Avipox Virus to Elicit Anti-Carcinoembryonic Antigen Immune Responses. J. Clin. Oncol. 18, 3964-3973 (2000).

Marshall, J. Carcinoembryoniec Antigen-Based Vaccines. Semin. Oncol. (suppl. 8): 30-36 (2003).

Miller, et al. Targeted Vectors for Gene Therapy. FASEB J. 9: 190-199 (1995).

Moingeon, et al. Cancer Vaccines. 19: 1305-1326 (2001).

Moingeon, et al. Strategies for Designing Vaccines Eliciting Th 1 Responses in Humans. J. Biotech. 98: 189-198 (2002).

Nestle, et al. Vaccination of Melanoma Patients with Peptide- or Tumor Lysate-Pulsed Dendritic Cells. Nature Med. vol. 4, No. 3, pp. 328-332 (1998).

Oertli et al. Rapid Induction of Specific Cytotoxic T Lymphocytes Against Melanoma-Associated Antigens by a Recombinant Vaccinia Virus Vector Expressing Multiple Immunodominant Epitopes and Costimulatory Molecules In Vivo, Human Gene Therapy, 13(4): 569-575 (Mar. 2002).

Pardoll, D,M. Cancer vaccines, Nat.Med. 4: 525-531 (1998).

Parkhurst, et al. Improved Induction of Melanoma-Reactive CTL with Peptides from Melanoma Antigen gp100 Modified at HLA-A0201-Binding Residues. J. Immunol. vol. 157, No. 6, pp. 2539-2548 (1996).

Parmiani, et al, Cancer Immunotherapy with Peptide-Based Vaccines: What Have We Achieved? Where Are We Going? J. Natl. Cancer Inst. 94: 805-818 (2002).

Phan, et al. Cancer Regression and Autoimmunity Induced by Cytotoxic T Lymphocyte-Associated Antigen 4 Blockade in Patients with Metastatic Melanoma, PNAS USA, 100(14): 8372-8377 (2003).

Quentin, et al. Adenovirus as an Expression Vector in Muscle Cells *in vivo*. PNAS USA, 89: 2581-2584 (1992).

Rao, et at. Partial Characterization of Two Subpopulations of T4 Cells Induced by Active Specific Intralymphatic Immunotherapy (ASILI) in Melanoma Patients. vol. 27, abstract 1290, p. 325 (1986).

Restifo, et al. Antigen Processing In Vivo and the Elicitation of Primary CTL Responses. J. Immunol, 154: 4414-4422 (1995).

Rosenberg, et al. Vitiligo in Patients with Melanoma: Normal Tissue Antigens Can Be Targets for Cancer Immunotherapy. J. Immunotherapy. 19(1): 81-84 (1996).

Rosenberg, et al. Immunologic and Therapeutic Evaluation of a Synthetic Peptide Vaccine for the Treatment of Patients with Metastatic Melanoma. *Nature Med*. 4: 321-327 (1998).

Rosenberg, S.A. Progress in Human Tumour Immunology and Immunotherapy. *Nature* 411, 380-384 (2001).

Spagnoli, et al. Cytotoxic T-cell Induction in Metastatic Melanoma Patients Undergoing Recombinant Vaccinia Virus-Based Immuno-Gene Therapy. Recent Results in Cancer Research, 160: 195-201 (2002).

Tartaglia, et al. Therapeutic Vaccines Against Melanoma and Colorectal Cancer. Vaccine, 19(17-19): 2571-2575 (2001).

Thomson, et al. Recombinant. Polyepitope Vaccines for the Delivery of Multiple CD8 Cytotoxic T Cell Epitopes. J. Immunol. 157: 822-826 (1996).

Tough, et al. Induction of Bystander T Cell Proliferation by Viruses and Type 1 Interferon In Vivo. Science, 272: 1947-1950 (1996).

Tsao, et al. Hypopigmentation Associated with an Adenovirus-Mediated gp100/MART-1-Transduced Dendritic Cell Vaccine for Metastatic Melanoma. Arch. Dermatol. 138: 799-802 (2002).

Van Den Eynde, et aI. A New Family of Genes Coding for an Antigen Recognized by Autologous Cytolytic T Lymphocytes on a Human Melanoma. J. Exp. Med. 182: 689-698 (1995).

Van Den Eynde, et al. T Cell Defined Tumor Antigens. Curr. Opin. Immunol. 9, 684-693 (1997).

Van Der Burg, et al. Induction of p53-Specific Immune Responses in Colorectal Cancer Patients Receiving a Recombinant ALVAC-p53 Candidate Vaccine. Clin. Cancer Res. 8: 1019-1027 (2002).

Velders, et al. Defined Flanking Spacers and Enhanced Proteolysis is Essential for Eradication of Established Tumors by an Epitope String DNA Vaccine. J. Immunol. 166: 5366-5373 (2001).

Von Mehren, et al. Pilot Study of a Dual Gene Recombinant Avipox Vaccine Containing Both Carcinoembryonic Antigen (CEA) and B7.1 Transgenes in Patients with Recurrent CEA-Expressing Adenocarcinomas. Clin. Cancer Res. 6: 2219-2228 (2000).

Von Mehren, et al. The Influence of Granulocyte Macrophate Colony-Stimulating Factor and Prior Chemotherapy on the immunological Response to a Vaccine (ALVAC-CEA B7.1) in Patients with Metastatic Melanoma. Clin. Cancer Res. 7: 1181-1191 (2001).

Wolfel, et al. Two Tyrosine Nonapeptides Recognized on HLA-A2 Melanomas by Autologous Cytolytic T Lymphocytes. Eur. J. Immunol. vol, 24, pp, 759-764 (1994).

* cited by examiner

Single Stranded Version of Nucleic Acid Insert of ALVAC recombinant (vCP1469A)
Coding for a MAGE 1/3 Minigene

```
         10        20        30        40        50        60        70        80        90       100       110       120
          •         •         •         •         •         •         •         •         •         •         •         •
AGCTTCTTATTCTATACTTAAAAAGTGAAATATAAATACAAAGGTTCTTGAGGGTTGTGTTAAATTGAAAGCGAGAAATAATCATAAATTATTTCATTATCGCGATATCCGTTAAGTTTG 130       140       150       160       170       180       190       200       210       220       230       240
          •         •         •         •         •         •         •         •         •         •         •         •
TATCUTAATGGAGTCCTTGCAGCTGGTCTTTGCCATTGACGTGAAGGAAGCAGACCCCCACCGGCCACTCCTATGTGCCTTGTCACCTGCCTAGGTCTCTGTCACCTATGATGGCCAATAAGCCGT.A.I 250       260       270       280       290       300       310
          •         •         •         •         •         •         •
AGAAGTGGACCCCATCGGCCACTTGTACTACCTCGAGGAATTCTTTTATTGATTAACTAGTCAAATGAGTAT      [SEQ ID NO:2]
```

* The sequence coding for the MAGE 1/3 Minigene polypeptide is bolded and italicized.

FIGURE 1

Polypeptide Encoded by the ALVAC(1)-MAGE-1/3 Minigene
Recombinant Viral Construct (vCP1469A)

MAGE-1, aa 149-181

MAGE-3, aa 161-169

SEQ ID NO:1    M E S L Q L V F G I D V K [E A D P T G H S Y] V L V T C L G L S Y D G N K R K [E V D P I G H L Y]

protease cleavage site

MAGE-specific antigen epitopes of MAGE-1 and -3 are boxed.

FIGURE 2

Capacity of the ALVAC(1)-MAGE 1/3 Minigene recombinant viral construct (vCP1469A) to express both the MAGE 1 and 3 specific antigen epitope Capacity of the MAGE-3 specific antigen epitope derived from the MAGE 1/3 Minigene to present in association with MHC I/HLA-B35 molecules

IMMUNOGENIC POLYPEPTIDES ENCODED BY MAGE MINIGENES AND USES THEREOF

CROSS-REFERENCE TO REALTED APPLICATIONS

This application is filed under 35 U.S.C. §371, and claims priority to International Application No. PCT/CA01/00646, filed May 7, 2001, which claims priority to U.S. Ser. No. 60/202,970 filed May 10, 2000; U.S. Ser. No. 60/203,578 filed May 11, 2000; and, U.S. Provisional Application No. 60/242,388 filed Oct. 20, 2000.

FIELD OF THE INVENTION

The present invention relates to immunology, in particular to novel polypeptides comprising several MAGE-specific antigen epitopes therein selected from different (i.e. discrete) members of the MAGE protein family, nucleic acids coding therefor, recombinant viruses comprising said nucleic acid, cells comprising said nucleic acids, compositions thereof, and their use as immunogenic agents.

BACKGROUND OF THE INVENTION

The prospects of cancer immunotherapy rely upon the identification of tumor associated antigens which can be recognized by the immune system. Specifically, target antigens eliciting T cell-mediated responses are of critical interest. This comes from evidence that cytotoxic T lymphocytes (CTLs) can induce tumor regression both in animal models (Kast W. et al (1989) Cell 59:6035; Greendberg P. (1991) Adv. Immunol. 49:281) and in humans (Boon T. et al. (1994) Annu. Rev. Immunol. 12:337). Antigens recognized, by CTLs consist of peptides originating from endogenous proteins presented in association with Major Histocompatibility Complex (MHC) molecules.

The first such human tumor associated antigen characterized was identified from a melanoma. This antigen (originally designated MAGE 1) was identified using CTLs isolated from an HLA A1+ melanoma patient to screen HLA A1 target cells transfected with tumor DNA (van der Bruggen P. (1991) Science 254:1643; said tumor associated antigens are now designated MAGE-A1, MAGE-A2, etc.—for purposes of this application the older designation will be adopted). Interestingly, MAGE 1 was found to belong to a family of at least 12 closely related genes located on the X chromosome (de Plaen, E. et al. (1994) Immunogenetics 40:360). The nucleic acid sequence of the 11 additional MAGE genes share 65-85% identity with that of MAGE-1 (de Smet, C. et al. (1994) Immunogenetics 39: 121). Both MAGE 1 and 3 are present in normal tissues, but expressed only in the testis (de Plaen, E. et al. (1994) Supra; de Smet, C. et al. (1994) Supra; Takahashi, K. et al. (1995) Cancer Res. 55:3478; Chomey, P. et al. (1995) Immunogenetics 43:97). These initial results have subsequently been extended with the identification of new gene families (i.e. RAGE, BAGE, GAGE), all of which are typically not expressed in normal tissues (except testis) but expressed in a variety of tumor types.

MAGE-1 and MAGE-3 are expressed in 48% and 76% of metastatic melanomas respectively (Brasseur, F. et al. (1995) IZnt. J Cancer 63:375), 35% and 30% of non-small cell lung cancer ("NSCLC"; Weynants, P. et al. (1994) Int. J. Cancer 56:826), 27% and 48% of head and neck squamous cell carcinomas (Eura, M. et al. (1995) Int. J. Cancer 64:304), 62% and 57% of esophageal squamous cell carcinomas (Inoue, H. et al. (1995) Int. J. Cancer 63:523), and 21% and 35% of bladder transitional cell carcinomas (Patard, J.-J. et al. (1995) Int. J. Cancer 64:60). They are also expressed (albeit less frequently) in tumors of other histological types such as breast tumors, soft tissue sarcomas and prostatic carcinoma (Brasseur, F. et al. (1992) Int. J Cancer 52:839; Van der Eynde et al. (1995) Curr. Opin. Immnunol. 7:674). The MAGE 3 gene is also expressed in colorectal carcinoma.

A number of immunogenic epitopes/peptides derived from MAGE proteins (in particular MAGE 1, 2 and 3) have been identified and characterized (reviewed in van der Eynde, B. J. and Boon, T. (1997) Int. J. Chem. Lab Res. 27:81). CTLs isolated from two melanoma patients were found to recognize MAGE-1 derived peptides presented in association with HLA-A1, B37 or Cw16 (Traversi, C. et al (1992) J. Exp. Med 176:1453; Tanzarella, S. et al. (1999) Cancer Res. 59:2668; van der Bruggen, P. et al. (1994) Eur. J I7 nmunol. 24:2134). In particular, the nonapeptide EADPTGHSY (SEQ ID NO: 5; amino acids 161-169 of MAGE 1) was demonstrated to be presented to cells of the immune system in association with the MHC class 1 molecule HLA-A1 (Traversi, C. et al. (1992) Supra). Synthetic peptides utilized to stimulate T cells have also facilitated the identification of a MAGE 1 epitope presented by HLA-A24 (Fujie, T et al. (1999) Int. J. Cancer 80:169).

It has also been demonstrated that MAGE-3 directs the expression of a number of antigens recognized by CTLs. For example, the nonapeptide EVDPIGHLY (SEQ ID NO: 6; amino acid 168-176 of MAGE 3) is recognized in association with the MHC class 1 molecule HLA-A1 (Gaugler, B. et al. (1994) J. Exp. Med. 179:921); the decapeptide MEVDPIGHLY (SEQ ID NO: 3; amino acids 167-176) in association with the MHC class 1 molecules HLA-B44.02 and HLA-B44.03 (Herman, J. et al. (1996) Iminunogenetics 43:377); the nonapeptide FLWGPRALV (SEQ ID NO: 4; amino acids 271-279) in association with the MHC class 1 molecule HLA-A2.01 (van der Bruggen, P. et al. (1994) Eur. J. Immunol. 24:3038). Furthermore, van der Bruggen and colleagues have identified six additional MAGE-derived epitopes that are presented to CTL in association with HLA-A3, A28, B7, B53, Cw2 and Cw3 (Chaux, P. et al. (1999) J1 mmunol. 163:2928; Luiten, R. et al. (2000), Tissue Antigens, 55: in press). Interestingly, it has recently been observed that an epitope of MAGE 1 previously identified as an epitope recognized by CTL in association with HLA-A1 can also be presented to CTL in association with both HLA-B3501 and B3503 (van der Bruggen, P. et al. (2000), submitted).

The present invention discloses novel polypeptides comprising several distinct MAGE-specific antigen epitopes selected from different (i.e. discrete) members of the MAGE protein family, nucleic acids coding therefor, recombinant viruses and/or cells comprising said nucleic acids, compositions of the aforementioned agents, and their advantageous use in generating MAGE-specific immune responses.

SUMMARY OF THE INVENTION

The present invention encompasses immunogenic peptides comprising several MAGE-specific antigen epitopes selected from different (i.e. discrete) members of the MAGE protein family, nucleic acids coding therefor, recombinant virus and/or cells comprising said nucleic acids, and compositions of the aforementioned. All of these aforementioned agents and compositions are characterized by their ability to induce or elicit an immune response against said polypeptide, a MAGE-specific antigen epitope of said polypeptide, a MAGE protein or fragment thereof comprising a MAGE-specific antigen epitope of said polypeptide, or cells binding and/or expressing the aforementioned polypeptide, MAGE-specific antigen epitope, MAGE protein polypeptide or fragment thereof.

Accordingly, in one aspect of the invention a polypeptide is provided wherein the MAGE-specific antigen epitopes are derived from MAGE 1, MAGE 2 and/or MAGE 3. Further aspects of the invention encompass polypeptides wherein said MAGE-specific antigen epitopes are directly adjoined together, or are joined via an amino acid linker sequence.

In a further aspect of the invention, the polypeptide comprises a first MAGE-specific antigen epitope derived from MAGE 1 having the amino acid sequence EADPTGHSY (SEQ ID NO: 5) and a second MAGE-specific antigen epitope derived from MAGE-3 having the amino acid sequence EVDPIGHLY (SEQ ID NO: 6). In yet further aspects, the polypeptide consists/comprises the amino acid sequence of SEQ ID NO: 1 (FIG. 2).

As previously noted, aspects of the invention encompass nucleic acids coding for the aforementioned polypeptides. Accordingly, aspects of the invention consist/comprise the nucleic acid sequence of SEQ ID NO:2 (FIG. 1). In further aspects of the invention, the nucleic acid is a DNA selected from the group consisting of viral nucleic acid, plasmid, bacterial DNA, naked/free DNA, and RNA. In yet further aspects, the viral nucleic acid is selected from the group consisting of adenovirus, alpha-virus and poxvirus. In still yet further embodiments, the poxvirus is selected from the group consisting of ALVAC, NYVAC, TROVAC and MVA.

Particular aspects of the invention further encompass recombinant viruses into which is inserted a nucleic acid encoding for a polypeptide of the invention, wherein the recombinant virus causes the expression of the polypeptide in an infected cell. In a further aspect of the invention, cells infected with said recombinant viruses are capable of eliciting an immune response directed against:
  (i) the polypeptide; and/or
  (ii) a MAGE-specific antigen epitope of the polypeptide; and/or
  (iii) a MAGE protein or fragment thereof comprising a MAGE-specific antigen epitope of the polypeptide; and/or
  (iv) cells expressing MAGE protein or fragments thereof, the polypeptide, a MAGE-specific antigen epitope of the polypeptide; and/or
  (v) cells binding said MAGE protein or fragments thereof, the polypeptide, a MAGE-specific antigen epitope of the polypeptide.

Further aspects of the invention encompass recombinant viruses selected from the group consisting of adenovirus, alphavirus and poxvirus; particular embodiments encompass ALVAC.

Further aspects of the invention encompass compositions of the aforementioned polypeptides, nucleic acids, and recombinant viruses. These compositions may optionally include adjuvants.

The invention further provides for cells comprising the aforementioned nucleic acid(s), wherein said cells express a polypeptide of the invention. In further aspects of the invention, the cells bind cleavage fragments of a polypeptide of the invention (these latter fragments optionally produced by a protease). In yet further aspects, the cells expressing the polypeptide also express a MHC HLA class 1 molecule. In still yet further aspects, the cells expressing the polypeptide are antigen-presenting cells.

The invention further provides a method of inducing an immune response in an animal directed against:
  (i) the polypeptide; and/or
  (ii) a MAGE-specific antigen epitope of the polypeptide; and/or
  (iii) a MAGE protein or fragment thereof comprising a MAGE-specific antigen epitope of the polypeptide; and/or
  (iv) cells expressing MAGE protein or fragments thereof, the polypeptide, a MAGE-specific antigen epitope of the polypeptide; and/or
  (v) cells binding said MAGE protein or fragments thereof, the polypeptide, a MAGE-specific antigen epitope of the polypeptide, comprising administering to said animal a polypeptide, or a nucleic acid, or a recombinant virus, or a cell of the invention in an amount sufficient to induce an immune response.

The invention in yet a further aspect provides for a treatment for cancer comprising any one of the aforementioned methods for inducing immune responses.

The invention in still a further aspect provides for the use of the polypeptides of the invention in the manufacture of a medicament for the treatment of cancer.

Other features and advantages of the present invention will become apparent from the following detailed description. It should be understood, however, that the detailed description and the specific examples while indicating particular embodiments of the invention are given by way of illustration only, since various changes and modifications within the spirit and scope of the invention will become apparent to those skilled in the art from this detailed description.

BRIEF DESCRIPTION OF THE FIGURES

The invention will be better understood with reference to the drawings in which:

FIG. 1 shows a single stranded DNA sequence comprising a MAGE 1/3 Minigene encoded thereby (SEQ ID NO:2) corresponding to the insert of the ALVAC(1)-MAGE 1/3 Minigene construct designated vCP1469A.

FIG. 2 shows the amino acid sequence (SEQ ID NO:1) of the MAGE 1/3 Minigene encoded by the DNA sequence of FIG. 1.

DETAILED DESCRIPTION OF THE INVENTION

Figure 3:
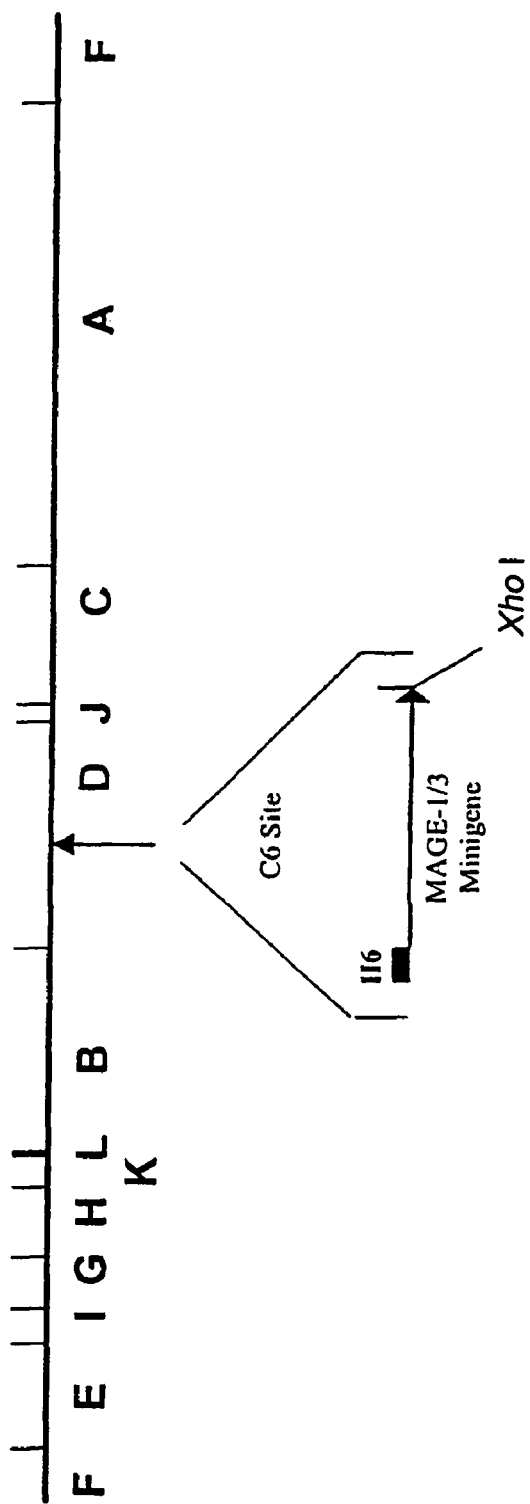
FIG. 3 depicts a schematic representation of the Xho I restriction map profile of the ALVAC(1)-MAGE 1/3 Minigene construct (vCP1469A).

The invention discloses immunogenic polypeptides comprising several MAGE-specific antigen epitopes selected from different (i.e. discrete) members of the MAGE protein family, nucleic acids coding therefor, recombinant viruses and/or cells comprising said nucleic acids (collectively designated as "agents" of the invention), and compositions of the aforementioned. All of the aforementioned agents and compositions of the invention have the ability to induce or elicit an immune response against said polypeptide, a MAGE-specific antigen epitope of said polypeptide, a MAGE protein or fragment thereof comprising a MAGE-specific antigen epitope of said polypeptide, or cells binding and/or expressing the aforementioned polypeptide, MAGE-specific antigen epitope, MAGE protein or fragment thereof. An "immune response" is defined as any response of the immune system, for example, of either a cell-mediated (i.e. cytotoxic T-lymphocyte mediated) or humoral (i.e. antibody mediated) nature.

Within the context of cell-mediated immune responses, tumor associated antigen proteins (such as members of the MAGE family) are processed by intracellular proteases into smaller epitope peptides which are subsequently transported to the cell surface tightly bound in a cleft on an MHC HLA class 1 molecule. T cells recognize these small epitope peptides only when presented in association with MHC HLA Class I molecules on the surface of appropriate cells. Analogously, in the context of humoral immune responses proteins can be processed into smaller epitope peptides which are subsequently presented on cell surfaces (i.e. antigen presenting cells) in association with MHC HLA class II molecules. Said complexes are recognized by appropriate cells of the humoral immune system.

As is well known to those skilled in the art, short peptides (i.e. epitopes) composed of amino acid sequences of about 9 to 12 amino acids derived from antigens are capable of binding directly within the cleft of an HLA class 1 molecule without intracellular processing. As previously noted, a number of such epitope peptides derived from MAGE proteins (i.e. MAGE-specific antigen epitopes) have been identified. Moreover, some of these MAGE-specific antigen epitopes have demonstrated the capacity to induce/elicit immune responses wherein appropriate MAGE-expressing target cells are lysed. The polypeptides of the present invention elicit an improved immune response to appropriate MAGE-expressing target cells by comparison to that observed when only a single MAGE-specific antigen epitope is employed as immunogen. Moreover, the appropriate choice of epitopes will provide the advantage of an immunogenic polypeptide capable of eliciting or inducing an immune response in a population of individuals not restricted to a single MHC HLA subclass. In addition, the linking of MAGE-specific antigen epitopes in a single polypeptide allows for the administration of a single immunogen to individuals (by contrast to a mixture of distinct individual peptides). As such, the polypeptide is appropriately processed to allow the individual MAGE-specific antigen epitopes encompassed therein to be presented in association with the relevant HLA class 1 molecules on relevant cell surfaces.

The individual MAGE-specific antigen epitopes which comprise the polypeptide of the present invention may each vary in the number of amino acids, typically comprising from about 8 to about 12 amino acids, but preferably of the size of 9 to 10 amino acids. In one embodiment of the invention, the MAGE-specific antigen epitopes each comprise 9 amino acids.

Any MAGE-specific antigen epitope derived from any member of the MAGE protein family can be incorporated into the polypeptides of the present invention. For example, a number of MAGE 1-specific antigen epitopes are disclosed in U.S. Pat. Nos. 5,405,940, 5,695,994, 5,843,448 and published PCT application WO 9504542; a number of MAGE 2-specific antigen epitopes are disclosed in U.S. Pat. Nos. 5,554,724, 5,686,068 and published PCT application WO 9525530; a number of MAGE 3-specific antigen epitopes are disclosed in U.S. Pat. Nos. 5,462,871, 6,025,474, 5,851,523, 5,965,535, 5,551,506, 5,591,430, 5,585,461 and published PCT applications WO 9525739, WO 9626214 and WO 9731017; and MAGE 6 specific antigen epitopes are disclosed in published PCT application WO 9810780 (all of which are herein incorporated by reference).

In one embodiment of the invention, the polypeptide comprises a first MAGE-specific antigen epitope selected from MAGE 1 and a second chosen from MAGE 3. In a further embodiment of the invention, the MAGE-1 specific antigen epitope comprises the amino acid sequence EADPTGHSY (SEQ ID NO: 5). The MAGE-3 specific antigen epitope may comprise the amino acid sequence EVDPIGHLY (SEQ ID NO: 6). It should be noted that the aforementioned epitopes encompassed by the polypeptide embodiments of this invention can be directly adjoined together, or be connected by an amino acid linker sequence. Said amino acid linker sequences for joining the MAGE-specific antigen epitopes may comprise from 1 to about 25 amino acids. In one embodiment, the linker comprises 16 amino acids. In further embodiments of the invention, the polypeptide and or amino acid linker sequence further comprises an amino acid sequence cleavable by proteolytic activity. A particular embodiment of the invention consists of the polypeptide whose sequence is denoted by SEQ ID NO:1 (FIG. 2).

The polypeptides of the present invention may also encompass "functionally equivalent variants" or "analogs" of the polypeptides. As such, this would include but not be limited to polypeptides with partial sequence homology, peptides having one or more specific conservative and/or non-conservative amino acid changes and peptide conjugates which do not alter the biological or structural properties of the polypeptide.

The polypeptides of the invention may be prepared using a variety of methods known to one skilled in the art. Accordingly, recombinant DNA methods can be utilized to provide these polypeptides. Nucleic acid sequences which encode for the polypeptides of the invention may be incorporated in a known manner into appropriate expression vectors (i.e. recombinant expression vectors). Possible expression vectors include (but are not limited to) cosmids, plasmids, or modified viruses (e.g. replication defective retroviruses, adenoviruses and adeno-associated viruses, lentiviruses, poxviruses), so long as the vector is compatible with the host cell used. The expression "vector is compatible with the host cell" is defined as contemplating that the expression vector(s) contain a nucleic acid molecule of the invention (hereinafter described) and attendant regulatory sequence(s) selected on the basis of the host cell(s) to be used for expression, said regulatory sequence(s) being operatively linked to the nucleic acid molecule. "Operatively linked" is intended to mean that the nucleic acid is linked to regulatory sequence(s) in a manner which allows expression of the nucleic acid. Suitable regulatory sequences may be derived from a variety of sources, including bacterial, fungal, or viral genes. (For example, see the regulatory sequences described in Goeddel, Gene Expression Technology: Methods in Enzymology 185, Academic Press, San Diego, Calif. (1990).) Selection of appropriate regulatory sequence(s) is dependent on the host cell(s) chosen, and may be readily accomplished by one of ordinary skill in the art. Examples of such regulatory sequences include the following: a transcriptional promoter and enhancer, RNA polymerase binding sequence, or a ribosomal binding sequence (including a translation initiation signal). Depending on the host cell chosen and the vector employed, other additional sequences (such as an origin of replication, additional DNA restriction sites, enhancers, and sequences conferring inducibility of transcription) may be incorporated into the expression vector.

The aforementioned expression vectors of the invention may also contain a selectable marker gene which facilitates the selection of host cells transformed or transfected with a recombinant molecule of the invention. Examples of selectable marker genes are genes encoding a protein such as G418 and hygromycin (which confer resistance to certain drugs), β-galactosidase, chloramphenicol acetyltransferase, or firefly luciferase.

Transcription of the selectable marker gene is monitored by changes in the concentration of the selectable marker protein such as β-galactosidase, chloramphenicol acetyltransferase, or firefly luciferase. Transformant cells can be selected with appropriate selection molecules if the selectable marker gene encodes a protein conferring antibiotic resistance (i.e. G418 in context of neomycin resistance). As is known to one skilled in the art, cells that have incorporated the selectable marker gene will survive, while cells which do not have any such incorporated detectable marker will die. This makes it possible to visualize and assay for expression from recombinant expression vectors of the invention. It will also be appreciated that selectable markers can be introduced on a separate vector from the nucleic acid of interest.

The recombinant expression vectors may also contain genes which encode a fusion moiety which provides increased expression of the polypeptides of the invention; increased solubility of the polypeptides of the invention; and/or aids in the purification of a target recombinant protein by acting as a ligand in affinity purification. For example, a proteolytic cleavage site may be added to the target recombinant polypeptide to allow separation of the recombinant polypeptide peptide(s) from the fusion moiety subsequent to purification of the fusion protein.

The polypeptides of the invention may also be prepared by chemical synthesis using techniques well known in the chemistry of proteins such as solid phase synthesis (Merrifield (1964). *J. Am. Chem. Assoc.* 85:2149) or synthesis in homogenous solution (Methods of Organic Chemistry, E. Wansch (Ed.) Vol. 15, pts. I and II, Thieme, Stuttgart (1987)).

Additional embodiments of the invention encompass nucleic acids coding for the polypeptides hereinbefore described. As defined herein, "nucleic acid(s)" encompass (but is not limited to) viral nucleic acid(s), plasmid(s), bacterial DNA, naked/free DNA and RNA. The nucleic acids encompass both single and double stranded forms. As such, these nucleic acids comprise the relevant base sequences coding for the aforementioned polypeptides. For purposes of definitiveness, the "relevant base sequences coding for the aforementioned polypeptides" further encompass complementary nucleic acid sequences.

In one embodiment of the invention, the nucleic acid has the sequence denoted by SEQ ID NO:2 (FIG. 1). In further embodiments of the invention, the nucleic acids comprise this sequence (i.e. SEQ ID NO:2 (FIG. 1)).

As stated above, the present invention the present invention also encompasses nucleic acid sequences which are complementary as well as anticomplementary to the sequence denoted by SEQ ID NO:2 and equivalent sequence variants thereof. One skilled in the art may be such complementary or anticomplementary nucleic acid sequences. Also as part of the invention are nucleic acid sequences which hybridize to one of the aforementioned nucleic acid molecules under stringent conditions. "Stringent conditions" as used herein refers to parameters with which the art is familiar and such parameters are discussed for example in Molecular Cloning: A Laboratory Manual, J. Sambrook, et al., eds., Second Edition, Cold Spring Harbor Laboratory Press, Cold Spring Harbor, New York, 1989 or Current Protocols in Molecular Biology, F. M. Ausubel, et al., eds., John Wiley & Sons Inc., New York. One skilled in the art would be able to identify homologs of nucleic acids encoding the MAGE polypeptides of the invention as well as screening cells and libraries for expression of such molecules which then are isolated, followed by isolated of the pertinent nucleic acid molecule and sequencing.

It is noted that the nucleic acid molecules described herein represent a preferred embodiment of the invention The invention also encompasses degenerate nucleic acids that differ from the aforementioned sequences. Due to degeneracy in the genetic code, variations in the DNA sequence will result in translation of equivalent peptides. It is thus understood that numerous choices of nucleotides may be made that will lead to a sequence capable of directing production of the polypeptides or functional analogs thereof of the present invention. As a result, substitutions are included in the scope of the invention.

The viral nucleic acid of the invention may be derived from a poxvirus or other virus such as adenovirus or alphavirus. As such, the viral nucleic acids fiber comprising a nucleic acid sequence coding for a polypeptide of the invention is designated for discussion hereinafter as a "viral vector". Preferably the viral vector is incapable of integration in recipient animal cells. The elements for expression from said vector may include a promoter suitable for expression in recipient animal cells.

Adenovirus vectors and methods for their construction have been described (e.g. U.S. Pat. Nos. 5,994,132, 5,932,210, 6,057,158 and Published PCT Applications WO 9817783, WO 9744475, WO 9961034, WO 9950292, WO 9927101, WO 9720575, WO 9640955, WO 9630534-all of which are herein incorporated by reference). Alphavirus vectors have also been described in the art and can be used in embodiments of this invention (e.g. U.S. Pat. Nos. 5,792,462, 5,739,026, 5,843,723, 5,789,245, and Published PCT Applications WO 9210578, WO 9527044, WO 9531565, WO 9815636-all of which are herein incorporated by reference), as have lentivirus vectors (e.g. U.S. Pat. Nos. 6,013,516, 5,994,136 and Published PCT Applications WO 9817816, WO 9712622, WO 9817815, WO 9839463, WO 9846083, WO 9915641, WO 9919501, WO 9930742, WO 9931251, WO 9851810, WO 0000600-all of which are herein incorporated by reference). Poxvirus vectors that can be used include, for example, vaccinia and canary poxvirus (as described in U.S. Pat. Nos. 5,364,773, 4,603,112, 5,762,938, 5,378,457, 5,494,807, 5,505,941, 5,756,103, 5,833,975 and 5,990,091-all of which are herein incorporated by reference). Poxvirus vectors comprising a nucleic acid coding for polypeptides of the invention can be obtained by homologous recombination as is known to one skilled in the art. As such, the polynucleotide of the invention is inserted into the viral genome under appropriate conditions for expression in mammalian cells (as described below).

In one embodiment of the invention the poxvirus vector is ALVAC (1) or ALVAC (2) (both of which have been derived from canarypox virus). ALVAC (1) (or ALVAC (2)) does not productively replicate in non-avian hosts, a characteristic thought to improve its safety profile. ALVAC (1) is an attenuated canarypox virus-based vector that was a plaque-cloned derivative of the licensed canarypox vaccine, Kanapox (Tartaglia et al. (1992) *Virology* 188:217; U.S. Pat. Nos. 5,505,941, 5,756,103 and 5,833,975-all of which are incorporated herein by reference). ALVAC (1) has some general properties which are the same as some general properties of Kanapox. ALVAC-based recombinant viruses expressing extrinsic immunogens have also been demonstrated efficacious as vaccine vectors (Tartaglia et al, In AIDS Research Reviews (vol. 3) Koff W., Wong-Staol F. and Kenedy R. C. (eds.), Marcel Dekker NY, pp. 361-378 (1993a); Tartaglia, J. et al. (1993b) *J. Virol.* 67:2370). For instance, mice immunized with an ALVAC (1) recombinant expressing the rabies virus glycoprotein were protected from lethal challenge with rabies virus (Tartaglia, J. et al., (1992) supra) demonstrating the potential for ALVAC (1) as a vaccine vector. ALVAC-based recombinants have also proven efficacious in dogs challenged with canine distemper virus (Taylor, J. et al. (1992) Virology 187:321) and rabies virus (Perkus, M. E. et al., In, Combined Vaccines and Simultaneous Administration: Current Issues and Perspective, Annals of the New York Academy of Sciences (1994)), in cats challenged with feline leukemia virus (Tartaglia, J. et al., (1993b) supra), and in horses challenged with equine influenza virus (Taylor, J. et al., In Proceedings of the Third International Symposium on Avian Influenza, Univ. of Wisconsin-Madison, Madison, Wis., pp. 331-335 (1993)).

ALVAC (2) is a second-generation ALVAC vector in which vaccinia transcription elements E3L and K3L have been inserted within the C6 locus (U.S. Pat. No. 5,990,091, incorporated herein by reference). The E3L encodes a protein capable of specifically binding to dsRNA. The K3L ORF has significant homology to E1F-2. Within ALVAC (2) the E3L gene is under the transcriptional-control of its natural promoter, whereas K3L has been placed under the control of the early/late vaccine H6 promoter. The E3L and K3L genes act to inhibit PKR activity in cells infected with ALVAC (II), allowing enhancement of the level and persistence of foreign gene expression.

Additional viral vectors encompass natural host-restricted poxviruses. Fowlpox virus (FPV) is the prototypic virus of the *Avipox* genus of the Poxviras family. Replication of avipox viruses is limited to avian species (Matthews, R. E. F. (1982) *Intervirology* 17:42) and there are no reports in the literature of avipox virus causing a productive infection in any non-avian species including man. This host restriction provides an inherent safety barrier to transmission of the virus to other species and makes use of avipox virus based vectors in veterinary and human applications an attractive proposition.

FPV has been used advantageously as a vector expressing immunogens from poultry pathogens. The hemagglutinin protein of a virulent avian influenza virus was expressed in an FPV recombinant. After inoculation of the recombinant into chickens and turkeys, an immune response was induced which was protective against either a homologous or a heterologous virulent influenza virus challenge (Taylor, J. et al. (1988) *Vaccine* 6: 504). FPV recombinants expressing the surface glycoproteins of Newcastle Disease Virus have also been developed (Taylor, J. et al. (1990) *J. Virol.* 64:1441; Edbauer, C. et al. (1990) *Virology* 179:901); U.S. Pat. No. 5,766,599-incorporated herein by reference).

A highly attenuated strain of vaccinia, designated MVA, has also been used as a vector for poxvirus-based vaccines. Use of MVA is described in U.S. Pat. No. 5,185,146. Other attenuated poxvirus vectors have been prepared via genetic modification to wild type strains of vaccinia. The NYVAC vector, for example, is derived by deletion of specific virulence and host-range genes from the Copenhagen strain of vaccinia (Tartaglia, J. et al. (1992), supra; U.S. Pat. Nos. 5,364,773 and 5,494,807-incorporated herein by reference) and has proven useful as a recombinant vector in eliciting a protective immune response against expressed foreign antigens.

Recombinant poxviruses can be constructed by a process known to those skilled in the art (as previously described for vaccinia and avipox viruses; U.S. Pat. Nos. 4,769,330; 4,722, 848; 4,603,112; 5,110,587; and 5,174,993-all of which are incorporated herein by reference).

As such, one embodiment of the invention encompasses a recombinant virus comprising a virus into which is inserted a nucleic acid encoding for a polypeptide of the invention, said recombinant virus causing the expression of the polypeptide in an infected cell. In further embodiments of the invention the recombinant virus is selected from the group consisting of adenovirus, alphavirus and poxvirus. In still further embodiments, the recombinant virus is ALVAC. In still yet a further embodiment of the invention, the recombinant virus is ALVAC(1) into which is inserted the nucleic acid of FIG. 1 (SEQ ID NO:2) coding for the polypeptide of FIG. 2 (SEQ ID NO:1). Additionally, the recombinant viral nucleic acid of said recombinant virus in one embodiment of the invention is further characterized in that it is schematically represented in FIG. 3.

Bacterial DNA useful in embodiments of the invention have also been disclosed and are known to those of ordinary skill in the art. These bacteria include, for example, *Shigella, Salmonella, Vibrio cholerae, Lactobacillus*, Bacille Calmette Guerin (BCG), and *Streptococcus*.

In further embodiments, live and/or attenuated bacteria per se may be used as vectors for nucleic acids of this invention. For example, non-toxicogenic *Vibrio cholerae* mutant strains may be useful as bacterial vectors in embodiments of this invention; as described in US Pat. No. 4,882,278 (disclosing a strain in which a substantial amount of the coding sequence of each of the two ctxA alleles has been deleted so that no functional cholera toxin is produced), WO 92/11354 (strain in which the irgA locus is inactivated by mutation; this mutation can be combined in a single strain with cixA mutations), and WO 94/1533 (deletion mutant lacking functional ctcA and attRS1 DNA sequences). These strains can be genetically engineered to express heterologous antigens, as described in WO 94/19482. (All of the aforementioned issued patent/patent applications are incorporated herein by reference.) An effective immunogen dose of a *Vibrio cholerae* strain capable of expressing a polypeptides encoded by a DNA molecule of the invention can contain, for example, about $1\times10^5$ to about $1\times10^9$, preferably about $1\times10^6$ to about $1\times10^8$ viable bacteria in an appropriate volume for the selected route of administration.

Attenuated *Salmonella typhimurium strains*, genetically engineered for recombinant expression of heterologous antigens and their use as oral immunogens are described, for example, in WO 92/11361.

As previously noted, those skilled in the art will readily recognize that other bacterial strains useful as sources of DNA and/or bacterial vectors in embodiments of this invention include *Shigella flexneri, Streptococcus gordonii*, and Bacille Calmette Guerin (as described in WO 88/6626, WO 90/0594, WO 91/13157, WO 92/1796, and WO 92/21376; all of which are incorporated herein by reference). In bacterial DNA embodiments of this invention, a nucleic acid of the invention may be inserted into the bacterial genome, can remain in a free state, or be carried on a plasmid.

Cells comprising the aforementioned nucleic acids coding for polypeptides of this invention encompass further embodiments of the invention. These cells encompass any potential cell into which a nucleic acid of this invention might be introduced and/or transfected. The choice of process for the introduction and/or transfection into cells is dependant upon the intrinsic nature of the nucleic acid (i.e. recombinant virus, plasmid), as will be known to one skilled in the art (for example, as taught in *Current Protocols in Molecular Biology*, F. M. Ausubel et al. (Eds.), John Wiley and Sons, Inc., N.Y., U.S.A. (1998), Chpt. 9; *Molecular Cloning: A Laboratory Manual* (2<sup>nd</sup> Ed.), J. Sambrook, E. F. Fritsch and T. Maniatis (Eds.), Cold Spring Harbor Laboratory Press, N.Y., U.S.A. (1989), Chpts. 1, 2, 3 and 16).

It is well documented that the class I and class II proteins of the major histocompatibility complex (MHC) performing a central immunological function in focusing T-lymphocytes of the immune system (i.e. CD8+ and CD4+ T lymphocytes). MHC class I proteins are expressed in nearly all nucleated cell types throughout the human body; MHC class II molecules are expressed mainly on antigen-presenting cells (APCs; namely mononuclear phagocytes, Langerhans-dendritic cells, and B lymphocytes). These distinct classes of cell surface molecules (i.e. class I and class II) present peptides/epitopes (derived from intracellular processing of protein antigens) to T lymphocytes (CD8+ and CD4+ T lymphocytes respectively) thus initiating both cellular and humoral immune responses. Generally, epitopes/peptides derived from alloantigens, tumor antigens or viruses will be presented in association with MHC class I molecules; extracellular antigens/proteins will be presented in association with MHC class II molecules. However, in some contexts endogenous antigens can also be presented in association with MHC class II molecules. [These general immunological principles are well described in the art-as, for example, in *Encyclopedia of Immunology* (2<sup>nd</sup> Ed.), Peter J. Delves (Ed.-in-Chief), Academic Press, San Diego, U.S.A., pp. 174-8, 191-8, 1108-13, 1690-709 (1998).]

As such, embodiments of the invention encompass cells into which has been introduced/transfected a nucleic acid of the invention, wherein said cells express a polypeptide of the invention. In further embodiments, said cells are capable of binding cleavage fragments (i.e. epitopes/peptides) of the polypeptide. In still yet further embodiments, these cleavage fragments are produced by a protease.

As conceived herein, embodiments of the invention may also encompass cells into which has been introduced/transfected a nucleic acid of the invention wherein said cells also express a MHC HLA molecule (i.e. class I and/or class II). In further embodiments, these cells are antigen-presenting cells, possibly selected from the group consisting of mononuclear phagocytes, Langerhans-dendritic cells ("dendritic cell(s)"), and B lymphocytes.

Additional embodiments of this invention further encompass pharmaceutical compositions comprising the aforementioned polypeptides of the invention, nucleic acids coding therefor, and/or recombinant viruses comprising said nucleic acids for administration to subjects in a biologically compatible form suitable for administration in vivo. By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of eliciting an immune response in a human. A therapeutically effective amount of a substance may vary according to factors such as the disease state/health, age, sex, and weight of the recipient, and the inherent ability of the particular polypeptide, nucleic acid coding therefor, or recombinant virus to elicit a desired immune response. Dosage regime may be adjusted to provide the optimum therapeutic response. For example, several divided doses may be administered daily or on at periodic intervals, and/or the dose may be proportionally reduced as indicated by the exigencies of the therapeutic situation.

The compositions described herein can be prepared by per se known methods for the preparation of pharmaceutically acceptable compositions which can be administered to subjects, such that an effective quantity of the active substance (i.e. composition) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Methods of inducing or eliciting an immune response in an animal directed against:
- a polypeptide of the invention, or
- a MAGE-specific antigen epitope of said polypeptide, or
- a MAGE protein or fragment thereof comprising a MAGE-specific antigen epitope, or
- cells expressing a MAGE protein or fragment thereof, the polypeptide of the invention, or a MAGE-specific antigen epitope of the polypeptide, or
- cells binding said: MAGE protein or fragment thereof, the polypeptide of the invention, or a MAGE-specific antigen epitope of the polypeptide, comprising the step of administering to said animal a polypeptide of the invention, a nucleic acid coding therefor, a recombinant virus comprising said nucleic acid, or a cell comprising said nucleic acid (or compositions of the aforementioned) are also within the scope of this invention. Further embodiments of this invention encompass treatments for cancer comprising the aforementioned methods of inducing or eliciting immune responses in animals.

As defined herein, a polypeptide of the invention, a nucleic acid coding therefor, a recombinant virus comprising said nucleic acid, a cell comprising said nucleic acid, and compositions of the aforementioned are collectively referred to as "immunizing agent(s)", "agent(s)", or "immunogen(s)".

As known to one of ordinary skill in the art, an animal may be immunized with a polypeptide of the invention, a nucleic acid coding therefor, a recombinant virus comprising said nucleic acid, or a cell comprising said nucleic acid (or compositions of the aforementioned) by any conventional route. This may include, for example, immunization via a mucosal surface (e.g., ocular, intranasal, oral, gastric, pulmonary, intestinal, rectal, vaginal, or urinary tract) or via a parenteral route (e.g., subcutaneous, intradermal, intramuscular, intravenous, or intraperitoneal). Preferred routes depend upon the choice of the immunogen (i.e. polypeptide vs. nucleic acid, composition formulation, etc.). The administration can be achieved in a single dose or repeated at intervals. The appropriate dosage is dependant on various parameters understood by the skilled artisans, such as the immunogen itself (i.e. polypeptide vs. nucleic acid (and more specifically type thereof)), the route of administration and the condition of the animal to be vaccinated (weight, age and the like). As such, embodiments of this invention encompass methods of eliciting immune responses in animals comprising administering an effective amount of a polypeptide of the invention, nucleic acid coding therefore, recombinant virus comprising said nucleic acid, or cells comprising said nucleic acid (or compositions of the aforementioned).

As noted, nucleic acids (in particular plasmids and/or free/naked DNA and/or RNA coding for the polypeptide of the invention) can be administered to an animal for purposes of inducing/eliciting an immune response (for example, US Pat. No. 5,589,466; McDonnell and Askari, *NEJM* 334:42-45 (1996); Kowalczyk and Ertl, *Cell Mol. Life Sci.* 55:751-770 (1999)). Typically, this nucleic acid is a form that is unable to replicate in the target animal's cell and unable to integrate in said animal's genome. The DNA/RNA molecule encoding the polypeptide is also typically placed under the control of a promoter suitable for expression in the animal's cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter. The desmin promoter is tissue-specific and drives expression in muscle cells. More generally, useful vectors have been described (i.e., WO 94/21797).

For administration of nucleic acids coding for a polypeptide of the invention, said nucleic acid can encode a precursor or mature form of the polypeptide. When it encodes a precursor form, the precursor form can be homologous or heterologous. In the latter case, a eucaryotic leader sequence can be used, such as the leader sequence of the tissue-type plasminogen factor (tPA).

Standard techniques of molecular biology for preparing and purifying nucleic acids well known to those skilled in the art can be used in the preparation of aspects of the invention (for example, as taught in *Current Protocols in Molecular Biology*, F. M. Ausubel et al. (Eds.), John Wiley and Sons, Inc, N.Y., U.S.A. (1998), Chpts. 1, 2 and 4; *Molecular Cloning: A Laboratory Manual* ($2^{nd}$ Ed.), J. Sambrook, E. F. Fritsch and T. Maniatis (Eds.), Cold Spring Harbor Laboratory Press, N.Y., U.S.A. (1989), Chpts. 1, 2, 3 and 7).

For use as an immunogen, a nucleic acid of the invention can be formulated according to various methods known to a skilled artisan. First, a nucleic acid can be used in a naked/free form, free of any delivery vehicles (such as anionic liposomes, cationic lipids, microparticles, (e.g., gold microparticles), precipitating agents (e.g., calcium phosphate) or any other transfection-facilitating agent. In this case the nucleic acid can be simply diluted in a physiologically acceptable solution (such as sterile saline or sterile buffered saline) with or without a carrier. When present, the carrier preferably is isotonic, hypotonic, or weakly hypertonic, and has a relatively low ionic strength (such as provided by a sucrose solution (e.g., a solution containing 20% sucrose)).

Alternatively, a nucleic acid can be associated with agents that assist in cellular uptake. It can be, i.e., (i) complemented with a chemical agent that modifies the cellular permeability (such as bupivacaine, see, for example, WO 94/16737), (ii) encapsulated into liposomes, or (iii) associated with cationic lipids or silica, gold, or tungsten microparticles.

Cationic lipids are well known in the art and are commonly used for gene delivery. Such lipids include Lipofectin (also known as DOTMA (N-[1-(2,3-dioleyloxy)propyl]-N,N,N-trimethylammonium chloride), DOTAP (1,2-bis(oleyloxy)-3-(trimethylammonium) propane). DDAB (dimethyldioctadecylammonium bromide), DOGS (dioctadecylamidologlycyl spermine) and cholesterol derivatives such as DC-Chol (3 beta-(N-(N,N'-dimethyl aminomethane)carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as, for example, described in WO 90/11092.

Other transfection-facilitating compounds can be added to a formulation containing cationic liposomes. A number of them are described in, for example, WO 93/18759, WO 93/19768, WO 94/25608, and WO 95/2397. They include, i.e., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery (as described in WO 91/359 and WO 93/17706). In this case, the microparticle-coated polynucleotides can be injected via intradermal or intraepidermal routes using a needleless injection device ("gene gun"), such as those described, for example, in U.S. Pat. No. 4,945,050, U.S. Pat. No. 5,015,580, and WO 94/24263.

Anionic and neutral liposomes are also well-known in the art (see, for example, Liposomes: A Practical Approach, RPC New Ed, IRL Press (1990), for a detailed description of methods for making liposomes) and are useful for delivering a large range of products, including polynucleotides.

As is well known to those of ordinary skill in the art, the ability of an agent to induce/elicit an immune response can be improved if, regardless of administration formulation (i.e. recombinant virus, nucleic acid, polypeptide), said agent is coadministered with an adjuvant. Adjuvants are described and discussed in "Vaccine Design-the Subunit and Adjuvant Approach" (edited by Powell and Newman, Plenum Press, New York, U.S.A., pp. 61-79 and 141-228 (1995)). Adjuvants typically enhance, the immunogenicity of an immunogen but are not necessarily immunogenic in and of themselves. Adjuvants may act by retaining the immunogen locally near the site of administration to produce a depot effect facilitating a slow, sustained release of immunizing agent to cells of the immune system. Adjuvants can also attract cells of the immune system to an immunogen depot and stimulate such cells to elicit immune responses. As such, embodiments of this invention encompass compositions further comprising adjuvants.

Desirable characteristics of ideal adjuvants include:
1) lack of toxicity;
2) ability to stimulate a long-lasting immune response;
3) simplicity of manufacture and stability in long-term storage;
4) ability to elicit both cellular and humoral responses to antigens administered by various routes, if required;
5) synergy with other adjuvants;
6) capability of selectively interacting with populations of antigen presenting cells (APC);
7) ability to specifically elicit appropriate $T_H 1$ or $T_H 2$ cell-specific immune responses; and
8) ability to selectively increase appropriate antibody isotype levels (for example, IgA) against antigens/immunogens.

However, many adjuvants are toxic and can cause undesirable side effects, thus making them unsuitable for use in humans and many animals. For example, some adjuvants may induce granulomas, acute and chronic inflammations (i.e. Freund's complete adjuvant (FCA)), cytolysis (i.e. saponins and pluronic polymers) and pyrogenicity, arthritis and anterior uveitis (i.e. muramyl dipeptide (MDP) and lipopolysaccharide (LPS)). Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection in vaccination contexts.

Adjuvants may be characterized as "intrinsic" or "extrinsic". Intrinsic adjuvants (such as lipopolysaccharides) are integral and normal components of agents which in themselves are used as vaccines (i.e. killed or attenuated bacteria). Extrinsic adjuvants are typically nonintegral immunomodulators generally linked to antigens in a noncovalent manner, and are formulated to enhance the host immune response.

A variety of potent extrinsic adjuvants have been described. These include (but are not limited to) saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

The use of saponins per se as adjuvants is also well known (Lacaille-Dubois, M. and Wagner, H. (1996) *Phytomedicine* 2:363). For example, Quil A (derived from the bark of the South American tree *Quillaja Saponaria Molina*) and fractions thereof has been extensively described (i.e. U.S. Pat. No. 5,057,540; Kensil, C. R. (1996) *Crit Rev Ther Drug Carrier Syst.* 12:1; and European Pat. EP 362279). The haemolytic saponins QS21 and QS17 (HPLC purified fractions of Quil A) have been described as potent systemic adjuvants (U.S. Pat. No. 5,057,540; European Pat. EP 362279). Also described in these references is the use of QS7 (a non-haemolytic fraction of Quil-A) which acts as a potent adjuvant for systemic vaccines. Use of QS21 is further described in Kensil et al. ((1991) *J. Immunol* 146:431). Combinations of QS21 and polysorbate or cyclodextrin are also known (WO 9910008). Particulate adjuvant systems comprising fractions of Quil A (such as QS21 and QS7) are described in WO 9633739 and WO 9611711.

Another preferred adjuvant/immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 9602555; European Pat. EP 468520; Davies et al. (1998) *J. Immunol* 160:87; McCluskie and Davis (1998) *J. Immunol.* 161:4463). In a number of studies, synthetic oligonucleotides derived from BCG gene sequences have also been shown to be capable of inducing immunostimulatory effects (both in vitro and in vivo; Krieg, (1995) *Nature* 374:546). Detailed analyses of immunostimulatory oligonucleotide sequences has demonstrated that the CG motif must be in a certain sequence context, and that such sequences are common in bacterial DNA but are rare in vertebrate DNA. (For example, the immunostimulatory sequence is often: purine, purine, C, G, pyrimidine, pyrimidine, wherein the CG motif is not methylated; however other unmethylated CpG sequences are known to be immunostimulatory and as such may also be used in the present invention.)

A variety of other adjuvants are taught in the art, and as such are encompassed by embodiments of this invention. U.S. Pat. No. 4,855,283 granted to Lockhoff et al. (incorporated herein by reference) teaches glycolipid analogues and their use as adjuvants. These include N-glycosylamides, N-glycosylureas and N-glycosylcarbamates, each of which is substituted in the sugar residue by an amino acid, as immunomodulators or adjuvants. Furthermore, Lockhoff et al. ((1991) *Chem. Int. Ed. Engl.* 30:1611) have reported that N-glycolipid analogs displaying structural similarities to the naturally-occurring glycolipids (such as glycophospholipids and glycoglycerolipids) are also capable of eliciting strong immune responses in both herpes simplex virus vaccine and pseudorabies virus vaccine.

U.S. Pat. No. 4,258,029 granted to Moloney (incorporated herein by reference) teaches that octadecyl tyrosine hydrochloride (OTH) functions as an adjuvant when complexed with tetanus toxoid and formalin inactivated type I, II and III poliomyelitis virus vaccine. Nixon-George et al. ((1990) *J. Immunol.* 14:4798) have also reported that octadecyl esters of aromatic amino acids complexed with a recombinant hepatitis B surface antigen enhanced the host immune responses against hepatitis B virus.

Adjuvant compounds may also be chosen from the polymers of acrylic or methacrylic acid and the copolymers of maleic anhydride and alkenyl derivative. Adjuvant compounds are the polymers of acrylic or methacrylic acid which are cross-linked, especially with polyalkenyl ethers of sugars or polyalcohol. These compounds are known by the term carbomer (Pharmeuropa Vol. 8, No. 2, June 1996). Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCL 9 g/l) all at once in several portions with concomitant or subsequent neutralization (pH 7.3 to 7.4), preferably with NaOH. This solution at physiological pH will be used as it is for mixing with the immunizing agent; said mixture being amenable to storage in the freeze-dried, liquid or frozen form.

Persons skilled in the art can also refer to U.S. Pat. No. 2,909,462 (incorporated herein by reference) which describes adjuvants encompassing acrylic polymers cross-linked with a polyhydroxylated compound having at least 3 hydroxyl groups (preferably not more than 8), the hydrogen atoms of the at least three hydroxyls being replaced by unsaturated aliphatic radicals having at least 2 carbon atoms. The preferred radicals are those containing from 2 to 4 carbon atoms (e.g. vinyls, allyls and other ethylenically unsaturated groups). The unsaturated radicals may themselves contain other substituents, such as methyl. The products sold under the name Carbopol (BF Goodrich, Ohio, USA) are particularly appropriate. They are cross-inked with allyl sucrose or with allyl pentaerythritol. Among them, there may be mentioned Carbopol (for example, 974P, 934P and 971P). Among the copolymers of maleic anhydride and alkenyl derivative, the copolymers EMA (Monsanto; which are copolymers of maleic anhydride and ethylene, linear or cross-linked, (for example cross-linked with divinyl ether)) are preferred. Reference may be made to J. Fields et al. ((1960) *Nature* 186: 778) for a further description of these chemicals (incorporated (herein by reference).

In further aspects of this invention, adjuvants useful for parenteral administration of immunizing agent include aluminum compounds (such as aluminum hydroxide, aluminum phosphate, and aluminum hydroxy phosphate; but might also be a salt of calcium, iron or zinc, or may be an insoluble suspension of acylated tyrosine, or acylated sugars, cationically or anionically derivatised polysaccharides, or polyphosphazenes). The antigen can be precipitated with, or adsorbed onto, the aluminum compound according to standard protocols well known to those skilled in the art.

Other adjuvants encompassed by embodiments of this invention include lipid A (in particular 3-de-O-acylated monophosphoryl lipid A (3D-MPL). 3D-MPL is a well known adjuvant manufactured by Ribi Innnunochem, Montana. Chemically it is often supplied as a mixture of 3-de-O-acylated monophosphoryl lipid A with 4, 5, or 6 acylated chains. It can be prepared by the methods taught in GB 2122204B. A is preferred form of 3D-MPL is in the form of a particulate formulation having a particle size less than 0.2 μm in diameter (European Pat. EP 689454).

Adjuvants for mucosal immunization may include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. A mutant having reduced toxicity may be used. Mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants include, for example Ser-63-Lys, Ala-69-Gly, Glu-110-Asp, and Glu-112-Asp mutants. Other adjuvants (such as a bacterial monophosphoryl lipid A (MPLA)) of various sources (e.g., *E. coli, Salmonella Minnesota, Salmonella typhimurium,* or *Shigella flexneri*) can also be used in the mucosal administration of immunizing agents.

Adjuvants useful for both mucosal and parenteral immunization include polyphosphazene (for example, WO 95/2415), DC-chol (3 b-(N-(N',N-dimethyl aminomethane)-carbamoyl) cholesterol (for example, U.S. Pat. No. 5,283,185 and WO 96/14831) and QS-21 (for example, WO 88/9336).

Adjuvants/immunostimulants as described herein may be formulated together with carriers, such as for example liposomes, oil in water emulsions, and/or metallic salts including aluminum salts (such as aluminum hydroxide). For example, 3D-MPL may be formulated with aluminum hydroxide (as discussed in EP 689454) or oil in water emulsions (as discussed in WO 9517210); QS21 may be advantageously formulated with cholesterol containing liposomes (as discussed in WO 9633739), in oil water emulsions (as discussed in WO 9517210) or alum (as discussed in WO 9815287). When formulated into vaccines, immunostimulatory oligonucleotides (i.e. CpGs) are generally administered in free solution together with free antigen (as discussed in WO 9602555; McCluskie and Davis (1998) Supra), covalently conjugated to an antigen (as discussed in WO 9816247), or formulated with a carrier such as aluminum hydroxide or alum (as discussed in Davies et al. Supra; Brazolot-Millan et al (1998) *Proc. Natl. Acad. Sci.* 95:15553).

Combinations of adjuvants/immunostimulants are also within the scope of this invention. For example, a combination of a monophosphoryl lipid A and a saponin derivative (as described in WO 9400153, WO 9517210, WO 9633739, WO 9856414, WO 9912565, WO 9911214) can be used, or more particularly the combination of QS21 and 3D-MPL (as described in WO 9400153). A combination of an immunostimulatory oligonucleotide and a saponin (such as QS21), or a combination of monophosphoryl lipid A (preferably 3D-MPL) in combination with an aluminum salt also form a potent adjuvant for use in the present invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of molecular genetics, protein biochemistry and immunology used but not explicitly described in this disclosure and these Examples are amply reported in the scientific literature and are well within the ability of those skilled in the art.

Example 1

Generation of the ALVAC-MAGE 1/3 Minigene Recombinant Construct (vCP1469A)

Summary

To generate the ALVAC-MAGE 1/3 Minigene recombinant designated vCP1469A, a nucleic acid containing a poxvirus-promoted expression cassette for a minigene consisting of MAGE 1 and MAGE 3 epitopes separated by a putative protease cleavage site was subcloned into an ALVAC donor plasmid. This expression cassette was subsequently inserted into the C6 insertion site in the ALVAC(1) genome by in vitro recombination.

No function has yet been ascribed to the C6 encoded polypeptide of ALVAC, nor does the deduced amino acid open reading frame encoded in this region share significant homology to any entry in the existing protein sequence databases. A schematic of the Xho I restriction map profile of the ALVAC(1)-MAGE 1/3 Minigene recombinant construct designated vCP1469A is shown in FIG. 3.

Generation of the vCP1469A ALVA C recombinant Plasmid pCDSRa (containing a sequence coding for a fragment of MAGE 1 encompassing amino acids 149-181) was used as a template in a PCR reaction with the following primers:

MAGE01 (SEQ ID NO: 8)
(5'>CCC TCG CGA TAT CCG TTA AGT TTG TAT CGT AAT GGA GTC CTT GCA GCT GGT C<C'), and

MAGE02 (SEQ ID NO: 9)
(5'>GGG GTC GAG CTA GTA CAA GTG GCC GAT GGG GTC CAG TTC TTT ACG CTT ATT GCC ATC ATA GGA GAG ACC TAG<3').

(This latter primer (i.e. MAGE02) comprises a nucleic acid antisense sequence for the MAGE 3-specific antigen epitope, proteolytic cleavage site, and the 6 terminal amino acids at the carboxyl end of the abovenoted fragment of MAGE 1.)

The resulting 180 by PCR fragment contained the 3' end of an H6 promoter (originating from plasmid pCDSRa) linked to a MAGE 1/3 fusion gene. The MAGE 1/3 fusion gene comprises the MAGE-1 specific antigen epitope (located within the MAGE-1 protein fragment consisting of amino acids 149-181), an engineered protease cleavage site and the MAGE-3 specific antigen epitope (amino acids 161-169 of MAGE-3; the sequence of these latter two provided by primer MAGE02 (as described above)). This fragment was digested with EcoR5 and Xho I and ligated with EcoR5/Xlo I digested plasmid pC6H6B7 (this latter plasmid contains an irrelevant H6-promoted coding sequence in a C6 donor plasmid). The resulting C6 donor plasmid (designated pMAGE1/3-1) contains a regenerated H6 promoter linked to the MAGE 1/3 Minigene.

DNA sequence analysis revealed a G to C substitution at position 118 of the fragment. To correct this nucleotide substitution, pMAGE 1/3-1 was used as a template for PCR amplification utilizing primers MAGE03 (SEQ ID NO: 10) (5'>ATC GCG ATA TCC GTT AAG TTT G<3') and MAGE04 (SEQ ID NO: 11) (5'>GGG CTC GAG CTA GTA CAA GTG GCC GAT GGG GTC CAC TTC TTT (5'>ATC GCG ATA TCC GTT AAG TTT G<3') and MAGE04 (SEQ ID NO: 11) (5'>GGG CTC GAG CTA GTA CAA GTG GCC GAT GGG GTC CAC TTC TTT ACG CTT ATT GCC<3'). The resulting 180 by fragment containing the (3') H6/MAGE-1/3 Minigene with corrected position 118 was digested with EcoR5 and Xho I and subsequently ligated with EcoR5/Xho I digested pMAGE 1/3-1 vector. The resulting C6 donor plasmid (designated pC6MAGE 1/3 CTL) contained the regenerated H6 promoter linked to the corrected MAGE 1/3 Minigene.

Recombination was preformed between donor plasmid pC6MAGE 1/3 CTL and ALVAC(1) rescuing virus utilizing procedures described in the art and known to skilled artisans (i.e. U.S. Pat. Nos. 4,769,330, 4,722,848, 4,603,112, 5,174,993, 5,110,587—all of which are incorporated herein by reference). The resultant recombinant virus (designated vCP1469A) comprises a vaccinia H6 promoted human MAGE 1/3 Minigene sequence in the C6 locus of ALVAC(1). It is characterized in that it comprises the nucleic acid insert whose sequence is depicted in FIG. 1 (SEQ ID NO:2) which codes for the polypeptide depicted in FIG. 2 (SEQ ID NO:1), and by the Xho I restriction map profile depicted in FIG. 3.

Verification of Insertion

Viral genomic DNA was isolated from cells infected with vCP1469A pursuant to methods well known to those skilled in the art (for example, as taught in Current Protocols in Molecular Biology, F. M. Ausubel et al. (Eds.), John Wiley and Sons, Inc., N.Y., U.S.A. (1998); Molecular Cloning: A Laboratory Manual (2"nd Ed.), J. Sambrook, E. F. Fritsch and T. Maniatis (Eds.), Cold Spring Harbor Laboratory Press, N.Y., U.S.A. (1989)). The genomic DNA was digested with restriction endonuclease Xho I. The resultant DNA fragments were fractionated by electrophoresis through an agarose gel and visualized by ethidium bromide staining. The insertion of the MAGE 1/3 Minigene expression cassette at the C6 locus was confirmed (see FIG. 3 for a schematic representation of the restriction map profile).

Example 2

Presentation of the Individual MAGE-Specific Antigen Epitopes of the MAGE1/3 Minigene in Suitable Target Cells The capacity of the ALVAC-MAGE 1/3 Minigene recombinant virus (i.e. vCP1469A) to express and appropriately present the MAGE-1 and MAGE-3 specific antigen epitopes in target cells has been analyzed using an in vitro assay system.

Human dendritic cells (DCs) were isolated from peripheral blood mononuclear cells via the culturing of non-adherent cells for 8 days in the presence of GM-CSF and IL4. Cells were harvested and incubated for 6 hours with recombinant virus (vCP1469A) at various multiplicities of infection (MOI; ranging from 0.9 to 60). Infected cells were washed and subsequently tested for their capacity to stimulate IFN-gamma release by either the CTL clone MZ2-CTL 82/30 (MAGE 1 specific, HLA-A1 restricted), or MZ2-CTL 20/38 (MAGE 3 specific, HLA-A1 restricted).

Figure 4:
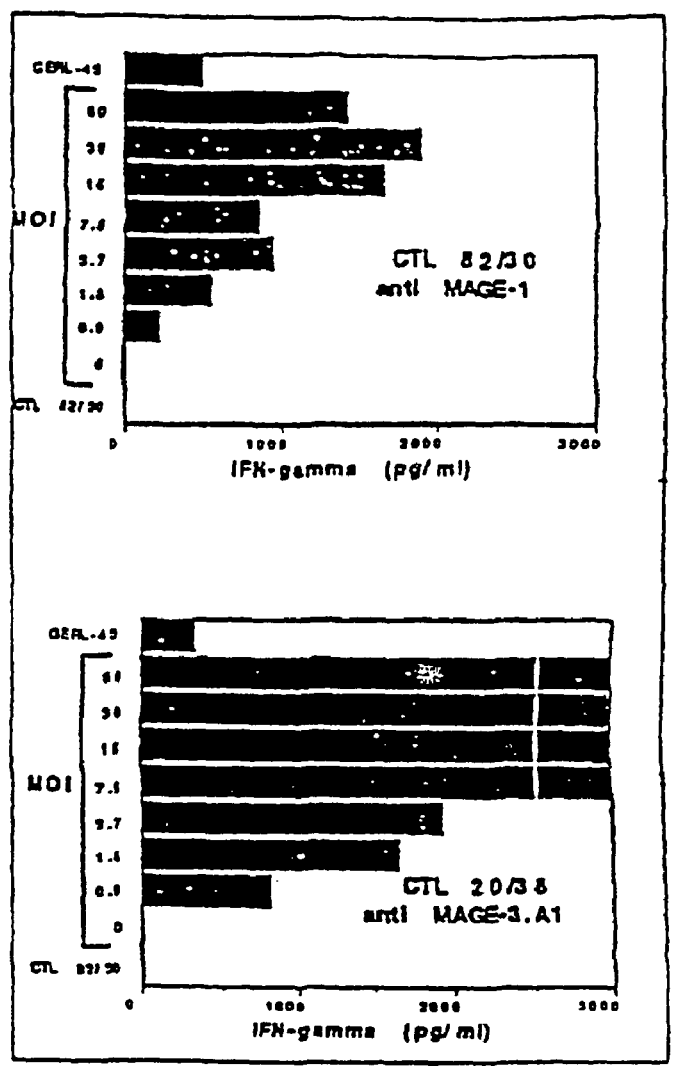
FIG. 4 shows data depicting the capacity of the ALVAC(1)-MAGE 1/3 Minigene construct (vCP1469A) of FIG. 3 to express both the MAGE 1 and 3 specific antigen epitope following infection of dendritic cells with recombinant virus comprising said ALVAC construct.

As depicted in FIG. 4, infected dendritic cells were able to induce significant production of IFN-gamma by both CTL clones, thus establishing that infection with the recombinant virus resulted in the processing and presentation of both the MAGE-1 and MAGE-3 specific antigen epitope. Uninfected dendritic cells did not induce the production of detectable IFN-gamma.

Example 3

Presentation of the MAGE-1 Specific Antigen Epitope Derived from the MAGE 1/3 Minigene in Association with Both MHC HLA-A1 and HLA-B35 Molecules Dendritic cells (DCs) of an HLA-A1 and B35 donor were infected with three different ALVAC recombinant viruses. The first virus contained the MAGE 1/3 Minigene (i.e. vCP1469A); the second contained the coding sequence of MAGE-1 (designated MAGE-A1); the third contained the coding sequence of β-galactosidase (designated βgal; negative control). DCs were distributed in microwells ($10^4$ cells per well), infected at various multiplicities of infection (MOI) for 2 hours, and subsequently washed. Melanoma cell lines MZ2-MEL.43 (HLA-A1$^+$, HLA-B35$^-$, MAGE-1$^+$) and MI13443-MEL (HLA-A1$^+$, HLA-B35$^+$, MAGE-1$^+$) were utilized as positive control target cells. Three thousand cells of CTL clone MZ2-CTL 82/30 (directed against the MAGE-1 epitope presented by HLA-A1) or CTL 7 (directed against the MAGE-1 epitope presented by HLA-B35) were added to the DCs or the positive control target cells. After 20 hours, IFN-γ produced by each CTL (indicative of an interaction between CTLs and target cells) was measured by ELISA.

Figure 5:
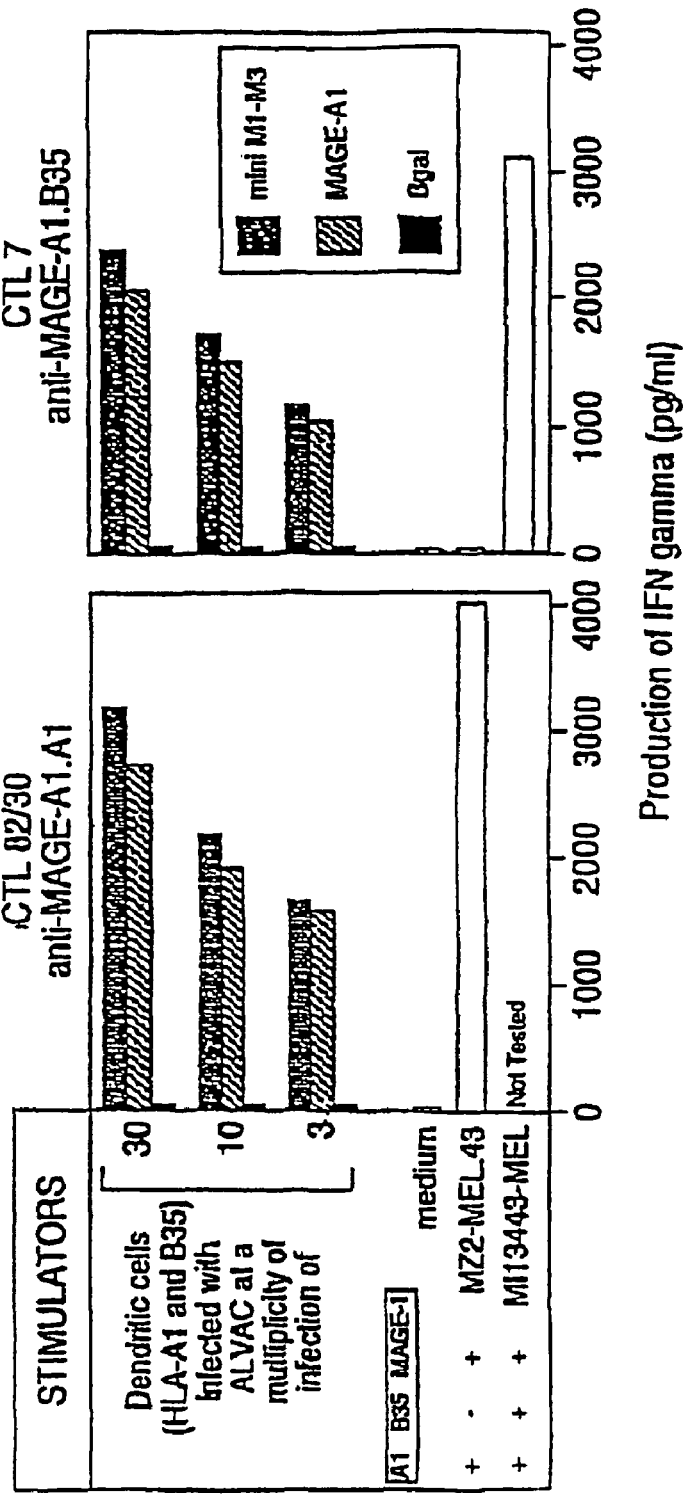
FIG. 5 shows data depicting the capacity of the MAGE 1 specific antigen epitope derived from the ALVAC(1)-MAGE 1/3 Minigene construct (vCP1469A) of FIG. 3 to present itself in association with both MHC HLA-A1 and HLA-B35 molecules.

As depicted in FIG. 5, infected DCs efficiently stimulated both relevant CTLs. The recognition of the epitope by CTL 7 was restricted by HLA-B35 molecules; the recognition of the epitope by MZ2-CTL 82/30 was restricted by HLA-A1. These results indicate that the MAGE-1 specific antigen epitope of vCP1469A is presented in association with both HLA-A1 and HLA-B35.

Example 4

Presentation of the MAGE-3 Specific Antigen Epitope Derived from the MAGE 1/3 Minigene in Association with MHC HLA-B35 Molecules Dendritic cells (DCs) of a B35 donor were infected with two different ALVAC recombinant viruses. The first virus contained the MAGE 1/3 Minigene (i.e. vCP1469A); the second contained the coding sequence of 13β-galactosidase (designated βgal; negative control). DCs were distributed in microwells ($10^4$ cells per well), infected at various multiplicities of infection (MOI) for 2 hours, and subsequently washed. The melanoma cell line MI13443-MEL (HLA-A1$^+$, HLAB35$^+$, MAGE-1$^+$) was utilized as a source of positive control target cells. Three thousand cells of CTL clone 41 (directed against the MAGE-3 epitope presented by HLA-B35) was added to the DCs or the positive control target cells. After 20 hours, IFN-y produced by each CTL (indicative of an interaction between CTLs and target cells) was measured by ELISA.

Figure 6:
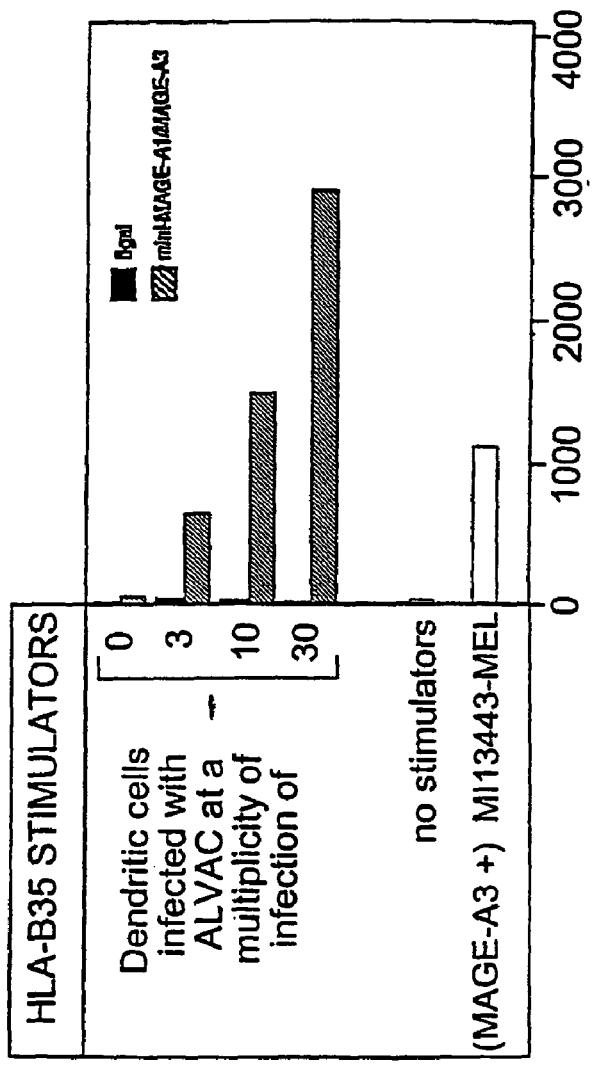
FIG. 6 shows data depicting the capacity of the MAGE 3 specific antigen epitope derived from the ALVAC(1)-MAGE1/3 Minigene construct (vCP1469A) of FIG. 3 to present itself in association with MHC HLAB35 molecules.

As depicted in FIG. 6, infected DCs efficiently stimulated CTL clone 41. These results indicate that the MAGE-3 specific antigen epitope of vCP1469A is presented in association with HLA-B35.

Example 5

Generation of a Clinical Response in a Human with Melanoma in Response to the Administration of an ALVA C-MA GE 1/3 Minigene Recombinant (vCP1469A)

The administration of the ALVAC(1)-MAGE 1/3 Minigene recombinant (vCP1469A) to a subject with melanoma (i.e. multiple cutaneous in-transit metastases of the right leg) encompassed a "prime-boost" methodology.

"Priming" involved 4 sequential injections of the aforementioned ALVAC recombinant at 3-week intervals; "boosting" involved 3 sequential injections of MAGE 1 and 3 specific antigen epitope peptides (i.e. EADPTGHSY (SEQ ID NO: 5) and EVDPIGHLY (SEQ ID NO: 6) respectively) at 3-week intervals commencing 3 weeks after the last injection with ALVAC recombinant.

In respect of ALVAC recombinant injections (i.e. priming), 1 ml of ALVAC recombinant ($10^{7.09}$ $CCID_{50}$) was divided between 4 injection sites—0.4 ml was injected subcutaneously at sites 1 and 3, and 0.1 ml injected intradermally at sites 2 and 4 (into the deltoid region or the anterior aspect of the thighs). No injection was given into limbs wherein draining lymph nodes were surgically removed and/or irradiated, or in limbs in which draining lymph nodes were known to contain metastases.

In respect of the MAGE-specific antigen epitope peptide injections (i.e. boosting), 0.5 ml of each peptide was divided between 2 separate injection sites—0.4 ml was injected subcutaneously at sites 1 and 3, and 0.1 ml injected intradermally at sites 2 and 4 (i.e. the boosting regiment with the 2 peptides consisted of 4 injection sites into the deltoid or anterior aspect of the thigh).

The recipient of the injections was routinely observed for a period of 120 minutes immediately following any injection. During these observation periods, arterial blood pressure (systolic and diastolic), heart rate and body oral temperature were measured every 30 minutes. The recipient was assessed every three weeks (with respect to history, physical examination, and basic biological tests). Color photographs were taken of all cutaneous and/or superficial lesions.

At the onset of the clinical trial, the recipient of the injections manifested melanoma in the form of multiple cutaneous in-transit metastases of the right leg. After receiving four series of injections with the ALVAC recombinant and 2 series of injections with the MAGE peptides, an objective regression of cutaneous metastases was observed. A minority of modules demonstrated some regression during the initial series of "priming" injections with the ALVAC recombinant. No new lesions have appeared, and bleeding lesions have resorbed. Most lesions decreased in size (mostly in depth); larger lesions became necrotic and gradually shrank. An enlargement of a right inguinal lymph node developed. An examination of said lymph node did not reveal the presence of melanoma cells.

Having illustrated and described the principles of the invention in a preferred embodiment, it should be appreciated by those skilled in the art that the invention can be modified in arrangement and detail without departure from such principles. We claim all modifications coming within the scope of the following claims. All publications, patents and patent application referred to herein, are herein incorporated by reference in their entirely to the same extent as if each individual publication, patent or patent application was specifically and individually indicated to the incorporated by reference in its entirety.

We claim:

1. An isolated nucleic acid molecule encoding a polypeptide comprising the amino acid sequence Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 2-34 of SEQ ID NO.: 1) and the amino acid sequence Glu Val Asp Pro Ile Gly His Leu Tyr (SEQ ID NO.:6).

2. An isolated nucleic acid molecule encoding a polypeptide comprising a first amino acid sequence Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 2-34 of SEQ ID NO.: 1), and a second amino acid sequence Glu Val Asp Pro Ile Gly His Leu Tyr (SEQ ID NO.:6), wherein the first and second amino acid sequences are separated by a protease cleavage site.

3. An isolated nucleic acid molecule encoding a polypeptide comprising the amino acid sequence Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 2-34 of SEQ ID NO.: 1), the amino acid sequence Asn Lys Arg Lys (amino acid residues 35-38 of SEQ ID NO.: 1), and the amino acid sequence Glu Val Asp Pro Ile Gly His Leu Tyr (SEQ ID NO.:6).

4. An isolated nucleic acid molecule encoding a polypeptide comprising a first amino acid sequence Met Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 1-34 of SEQ ID NO.: 1) and a second amino acid sequence Glu Val Asp Pro Ile Gly His Leu Tyr (SEQ ID NO.:6), wherein the first and second amino acid sequences are separated by a protease cleavage site.

5. An isolated nucleic acid molecule encoding a polypeptide comprising the amino acid sequence Met Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 1-34 of SEQ ID NO.: 1), the amino acid sequence Asn Lys Arg Lys (amino acid residues 35-38 of SEQ ID NO.: 1), and the amino acid sequence Glu Val Asp Pro Ile Gly His Leu Tyr (SEQ ID NO.:6).

6. An isolated nucleic acid molecule encoding a polypeptide comprising a first amino acid sequence Glu Ala Asp Pro Thr Gly His Ser Tyr (SEQ ID NO.: 5), a second amino acid sequence Asn Lys Arg Lys (amino acid residues 35-38 of SEQ ID NO.: 1), and a third amino acid sequence Glu Val Asp Pro Ile Gly His Leu Tyr (SEQ ID NO.: 6).

7. An isolated nucleic acid molecule comprising SEQ ID NO.: 2.

8. The isolated nucleic acid molecule of SEQ ID NO. 2.

9. A recombinant expression vector comprising a nucleic acid molecule encoding a polypeptide selected from the group consisting of:

(a) a polypeptide comprising the amino acid sequence Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 2-34 of SEQ ID NO.: 1) and the amino acid sequence Glu Val Asp Pro Ile Gly His Leu Tyr (SEQ ID NO.:6);

(b) a polypeptide comprising a first amino acid sequence Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 2-34 of SEQ ID NO.: 1) and a second amino acid sequence Glu Val Asp Pro Ile Gly His Leu Tyr (SEQ ID NO.:6), wherein the first and second amino acid sequences are separated by a protease cleavage site;

(c) a polypeptide comprising the amino acid sequence Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 2-34 of SEQ ID NO.: 1), the amino acid sequence Asn Lys Arg Lys (amino acid residues 35-38 of SEQ ID NO.: 1), and the amino acid sequence Glu Val Asp Pro Ile Gly His Leu Tyr (SEQ ID NO.:6);

(d) a polypeptide comprising a first amino acid sequence Met Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 1-34 of SEQ ID NO.: 1) and a second amino acid sequence Glu Val Asp Pro Ile Gly His Leu Tyr (SEQ ID NO.:6), wherein the first and second amino acid sequences are separated by a protease cleavage site;

(e) a polypeptide comprising the amino acid sequence Met Glu Ser Leu Gln Leu Val Phe Gly Ile Asp Val Lys Glu Ala Asp Pro Thr Gly His Ser Tyr Val Leu Val Thr Cys Leu Gly Leu Ser Tyr Asp Gly (amino acid residues 1-34 of SEQ ID NO.: 1), the amino acid sequence Asn Lys Arg Lys (amino acid residues 35-38 of SEQ ID NO.: 1), and the amino acid sequence Glu Val Asp Pro Ile Gly His Leu Tyr (SEQ ID NO.:6); and, (f) a polypeptide comprising a first amino acid sequence Glu Ala Asp Pro Thr Gly His Ser Tyr (SEQ ID NO.: 5), a second amino acid sequence Asn Lys Arg Lys (amino acid residues 35-38 of SEQ ID NO.: 1), and a third amino acid sequence Glu Val Asp Pro Ile Gly His Leu Tyr (SEQ ID NO.: 6).

10. The recombinant expression vector of claim 9 wherein the expression vector is selected from the group consisting of a cosmid, plasmid, and a viral vector.

11. The recombinant expression vector of claim 10 wherein the viral vector is selected from the group consisting of adenovirus, alphavirus and poxvirus.

12. The recombinant expression vector of claim 11 wherein the poxvirus is ALVAC or ALVAC(2).

13. A composition comprising a recombinant expression vector of claim 9 and a pharmaceutically acceptable vehicle or diluent.

14. The composition of claim 13 further comprising an adjuvant.

* * * * *

SEQUENCE LISTING

<160> NUMBER OF SEQ ID NOS: 11

<210> SEQ ID NO 1
<211> LENGTH: 47
<212> TYPE: PRT
<213> ORGANISM: Homo sapiens

<400> SEQUENCE: 1

```
Met Glu Ser Leu Gln Leu Val Phe Gly Ile Asp Val Lys Glu Ala Asp
1               5                   10                  15

Pro Thr Gly His Ser Tyr Val Leu Val Thr Cys Leu Gly Leu Ser Tyr
            20                  25                  30

Asp Gly Asn Lys Arg Lys Glu Val Asp Pro Ile Gly His Leu Tyr
        35                  40                  45
```

<210> SEQ ID NO 2
<211> LENGTH: 313
<212> TYPE: DNA
<213> ORGANISM: Homo sapiens

<400> SEQUENCE: 2

```
agcttcttta ttctatactt aaaaagtgaa aataaataca aaggttcttg agggttgtgt      60
taaattgaaa gcgagaaata atcataaatt atttcattat cgcgatatcc gttaagtttg     120
tatcgtaatg gagtccttgc agctggtctt tggcattgac gtgaaggaag cagacccac     180
```

```
cggccactcc tatgtgcttg tcacctgcct aggtctctcc tatgatggca ataagcgtaa      240
agaagtggac cccatcggcc acttgtacta cctcgaggaa ttcttttat tgattaacta       300 gtcaaatgag tat                                                         313
```

<210> SEQ ID NO 3
<211> LENGTH: 10
<212> TYPE: PRT
<213> ORGANISM: Homo sapiens

<400> SEQUENCE: 3

```
Met Glu Val Asp Pro Ile Gly His Leu Tyr
1               5                   10
```

<210> SEQ ID NO 4
<211> LENGTH: 9
<212> TYPE: PRT
<213> ORGANISM: Homo sapiens

<400> SEQUENCE: 4

```
Phe Leu Trp Gly Pro Arg Ala Leu Val
1               5
```

<210> SEQ ID NO 5
<211> LENGTH: 9
<212> TYPE: PRT
<213> ORGANISM: Homo sapiens

<400> SEQUENCE: 5

```
Glu Ala Asp Pro Thr Gly His Ser Tyr
1               5
```

<210> SEQ ID NO 6
<211> LENGTH: 9
<212> TYPE: PRT
<213> ORGANISM: Homo sapiens

<400> SEQUENCE: 6

```
Glu Val Asp Pro Ile Gly His Leu Tyr
1               5
```

<210> SEQ ID NO 7
<211> LENGTH: 141
<212> TYPE: DNA
<213> ORGANISM: Homo sapiens

<400> SEQUENCE: 7

```
atggagtcct tgcagctggt ctttggcatt gacgtgaagg aagcagaccc caccggccac      60
tcctatgtgc ttgtcacctg cctaggtctc tcctatgatg gcaataagcg taaagaagtg     120
gaccccatcg gccacttgta c                                                141
```

<210> SEQ ID NO 8
<211> LENGTH: 51
<212> TYPE: DNA
<213> ORGANISM: Artificial Sequence
<220> FEATURE:
<223> OTHER INFORMATION: primer

<400> SEQUENCE: 8

```
ccctcgcgat atccgttaag tttgtatcgt aatggagtcc ttgcagctgg t               51
```

<210> SEQ ID NO 9
<211> LENGTH: 72

-continued

```
<212> TYPE: DNA
<213> ORGANISM: Artificial Sequence
<220> FEATURE:
<223> OTHER INFORMATION: Homo sapiens

<400> SEQUENCE: 9
gggctcgagc tagtacaagt ggccgatggg gtccagttct ttacgcttat tgccatcata      60
ggagagacct ag                                                          72

<210> SEQ ID NO 10
<211> LENGTH: 22
<212> TYPE: DNA
<213> ORGANISM: Artificial
<220> FEATURE:
<223> OTHER INFORMATION: Homo sapiens

<400> SEQUENCE: 10
atcgcgatat ccgttaagtt tg                                               22

<210> SEQ ID NO 11
<211> LENGTH: 54
<212> TYPE: DNA
<213> ORGANISM: Artificial Sequence
<220> FEATURE:
<223> OTHER INFORMATION: Homo sapiens

<400> SEQUENCE: 11
gggctcgagc tagtacaagt ggccgatggg gtccacttct ttacgcttat tgcc            54
```